(12) United States Patent
Schwarz et al.

(10) Patent No.: US 9,920,371 B2
(45) Date of Patent: Mar. 20, 2018

(54) SCREENING METHOD

(71) Applicant: Medvet Science Pty. Ltd., Underdale (AU)

(72) Inventors: Quenten Philip Schwarz, Joslin (AU); Angel Francisco Lopez, Medindie (AU)

(73) Assignee: Medvet Sciences Pty. Ltd., Underdale (AU)

( * ) Notice: Subject to any disclaimer, the term of this patent is extended or adjusted under 35 U.S.C. 154(b) by 0 days.

(21) Appl. No.: 14/346,292

(22) PCT Filed: Sep. 21, 2012

(86) PCT No.: PCT/AU2012/001141
§ 371 (c)(1),
(2) Date: Mar. 20, 2014

(87) PCT Pub. No.: WO2013/040650
PCT Pub. Date: Mar. 28, 2013

(65) Prior Publication Data
US 2014/0237630 A1 Aug. 21, 2014

(30) Foreign Application Priority Data
Sep. 22, 2011 (AU) ................ 2011903906

(51) Int. Cl.
*G01N 33/53* (2006.01)
*G01N 33/566* (2006.01)
*C12Q 1/68* (2018.01)
*G01N 33/68* (2006.01)
*C07K 14/47* (2006.01)
*G01N 33/50* (2006.01)

(52) U.S. Cl.
CPC ........ *C12Q 1/6883* (2013.01); *C07K 14/4705* (2013.01); *G01N 33/5088* (2013.01); *G01N 33/6893* (2013.01); *G01N 33/6896* (2013.01); *G01N 2333/4706* (2013.01); *G01N 2500/00* (2013.01); *G01N 2800/30* (2013.01); *G01N 2800/302* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2002/0120947 A1 8/2002 Roch et al.
2005/0009094 A1 1/2005 Mueller et al.

FOREIGN PATENT DOCUMENTS

| CN | 102099492 A | 6/2011 |
|---|---|---|
| CN | 102146367 A | 8/2011 |
| WO | WO 2009/048747 A2 | 4/2009 |
| WO | WO 2009/138499 | 11/2009 |

OTHER PUBLICATIONS

He et al., J. Proteome Research, 2010, 9: 6180-90.*
Cheah et al., "Neurodevelopmental and neuropsychiatric behaviour defects arise from 14-3-3ζ deficiency," Molecular Psychiatry, 17:451-466 (2012).
Middleton et al., "Altered Expression of 14-3-3 Genes in the Prefrontal Cortex of Subjects with Schizophrenia," Neuropsychopharmacology, 30:974-983 (2005).
Yang, "Developmental deregulation and tumorigenesis inhibition in 14-3-3zeta knockout mouse," University of Texas GSBS Dissertations and Theses (Open Access), Paper 175, Aug. 2011.
International Search Report for PCT/AU2012/001141 dated Oct. 16, 2012.
Aitken, "14-3-3 proteins: a historic overview," Seminars in Cancer Biology, 16(3):162-172 (Jun. 2006).

(Continued)

*Primary Examiner* — Olga N Chernyshev
(74) *Attorney, Agent, or Firm* — Knobbe Martens Olson & Bear LLP

(57) ABSTRACT

The present invention provides a method of screening a mammal for the onset or predisposition to the onset of a neuropsychiatric disorder. More particularly, the present invention provides a method of screening a mammal for the onset or predisposition to the onset of schizophrenia by screening for a decrease in the functional level of protein 14-3-3ζ. In a related aspect, the present invention also provides a means of monitoring a patient diagnosed with a neuropsychiatric disorder, such as schizophrenia, by screening for changes to functional levels of protein 14-3-3ζ. This may be useful, for example, in the context of evaluating the effectiveness of a prophylactic or therapeutic treatment regime or otherwise monitoring the impact of physiological or metabolic changes which may occur in a patient. The method of the present invention is useful in a wide range of applications including, inter alia, providing a means of identifying mammals susceptible to the onset of a neuropsychiatric condition, such as a condition characterized by one or more symptoms of schizophrenia, thereby enabling the implementation of prophylactic or early therapeutic intervention in an effort to either minimize or prevent the onset of the condition. It also provides a means of confirming diagnoses which would otherwise be based solely on an assessment of positive and negative symptoms.

2 Claims, 18 Drawing Sheets

(56) References Cited

OTHER PUBLICATIONS

Alon et al., "Broad patterns of gene expression revealed by clustering analysis of tumor and normal colon tissues probed by oligonucleotide arrays," Proceedings of the National Academy of Sciences USA, 96(12):6745-6750 (Jun. 1999).
Baxter et al., "Immunolocalisation of 14-3-3 isoforms in normal and scrapie-infected murine brain," Neuroscience, 109(1):5-14 (Jan. 2002).
Berg et al., "14-3-3 proteins in the nervous system," Nature Reviews Neuroscience, 4(9):752-762 (Sep. 2003).
Bradshaw et al., "DISC1-binding proteins in neural development, signalling and schizophrenia," Neuropharmacology, 62(3):1230-1241 (Mar. 2012).
Brenner et al., "Encoded combinatorial chemistry," Proceedings of the National Academy of Sciences USA, 89(12):5381-5383 (Jun. 1992).
Christian et al., "Simplified methods for construction, assessment and rapid screening of peptide libraries in bacteriophage," Journal of Molecular Biology, 227(3):711-718 (Oct. 1992).
Clark et al., "DNA methylation: bisulphite modification and analysis," Nature Protocols, 1(5):2353-2364 (Dec. 2006).
Coyle et al., "Maternal dietary zinc supplementation prevents aberrant behaviour in an object recognition task in mice offspring exposed to LPS in early pregnancy," Behavioural Brain Research, 197(1):210-218 (Jan. 2009).
De Bruin et al., "Beneficial effects of galantamine on performance in the object recognition task in Swiss mice: deficits induced by scopolamine and by prolonging the retention interval," Pharmacology Biochemistry and Behavior, 85(1):253-260 (Sep. 2006).
Dere et al., "The case for episodic memory in animals," Neuroscience and Biobehavioral Reviews, 30(8):1206-1224 (Dec. 2006).
Devlin et al., "Random peptide libraries: a source of specific protein binding molecules," Science, 249(4967):404-406 (Jul. 1990).
Eichler et al., "Peptide, peptidomimetic, and organic synthetic combinatorial libraries," Medicinal Research Reviews, 15(6):481-496 (Nov. 1995).
English et al., "The neuroproteomics of schizophrenia," Biological Psychiatry, 69(2):163-172 (Jan. 2011).
Erb et al., "Recursive deconvolution of combinatorial chemical libraries," Proceedings of the National Academy of Sciences USA, 91(24):11422-11426 (Nov. 1994).
Fodor et al., "Light-directed, spatially addressable parallel chemical synthesis," Science, 251(4995):767-773 (Feb. 1991).
Forwood et al., "Hippocampal lesions that abolish spatial maze performance spare object recognition memory at delays of up to 48 hours," Hippocampus, 15(3):347-355 (Jan. 2005).
Francis et al., "Combinatorial libraries of transition-metal complexes, catalysts and materials," Current Opinion in Chemical Biology, 2(3):422-428 (Jun. 1998).
Fu et al., "14-3-3 proteins: structure, function, and regulation," Annual Review of Pharmacology and Toxicology, 40(1):617-647 (Apr. 2000).
Gallop et al., "Applications of combinatorial technologies to drug discovery. 1. Background and peptide combinatorial libraries," Journal of Medicinal Chemistry, 37(9):1233-1251 (Apr. 1994).
Germer et al., "High-throughput SNP allele-frequency determination in pooled DNA samples by kinetic PCR," Genome Research, 10(2):258-266 (Feb. 2000).
Gordon et al., "Applications of combinatorial technologies to drug discovery. 2. Combinatorial organic synthesis, library screening strategies, and future directions," Journal of Medicinal Chemistry, 37(10):1385-1401 (May 1994).
Gordon et al., "Strategy and tactics in combinatorial organic synthesis. Applications to drug discovery," Accounts of Chemical Research, 29(3):144-154 (Mar. 1996).
Guo et al., "Direct fluorescence analysis of genetic polymorphisms by hybridization with oligonucleotide arrays on glass supports," Nucleic Acids Research, 22(24):5456-5465 (Jan. 1994).
Guthridge et al., "The phosphoserine-585—dependent pathway of the GM-CSF/IL-3/IL-5 receptors mediates hematopoietic cell survival through activation of NF-κB and induction of bcl-2," Blood, 103(3):820-827 (Feb. 2004).
Heid et al., "Real time quantitative PCR," Genome Research, 6(10):986-994 (Oct. 1996).
Houghten el al., "Generation and use of synthetic peptide combinatorial libraries for basic research and drug discovery," Nature, 354(6348):84-86 (Nov. 1991).
Houghten et al., "The use of synthetic peptide combinatorial libraries for the identification of bioactive peptides," Biotechniques, 13(3):412-421 (Sep. 1992) (Abstract).
Jayawickreme et al., "Creation and functional screening of a multiuse peptide library," Proceedings of the National Academy of Sciences USA, 91(5):1614-1618 (Mar. 1994).
Jia, Yanbin et al., "An association study between polymorphisms in three genes of 14-3-3 (tyrosine 3-monooxygenase/tryptophan 5-monooxygenase activation protein) family and paranoid schizophrenia in northern Chinese population" European Psychiatry, Oct. 2004, pp. 377-379, vol. 19, No. 6.
Kaech et al., "Culturing hippocampal neurons," Nature Protocols, 1(5):2406-2415 (Dec. 2006).
Kay et al., "An M13 phage library displaying random 38-amino-acid peptides as a source of novel sequences with affinity to selected targets," Gene, 128(1):59-65 (Jun. 1993).
Komada et al., "Elevated plus maze for mice," JoVE (Journal of Visualized Experiments), (22):e1088-e1088 (Dec. 2008).
Lam et al., "A new type of synthetic peptide library for identifying ligand-binding activity," Nature, 354(6348):82-84 (Nov. 1991).
Lenstra et al., "Isolation of sequences from a random-sequence expression library that mimic viral epitopes," Journal of Immunological Methods, 152(2):149-157 (Aug. 1992).
Lister, "The use of a plus-maze to measure anxiety in the mouse," Psychopharmacology, 92(2):180-185 (Jun. 1987).
Martins-De-Souza et al., "Proteome analysis of schizophrenia brain tissue," The World Journal of Biological Psychiatry, 11(2):110-120 (Jan. 2010).
Maskos et al., "Oligonucleotide hybridisations on glass supports: a novel linker for oligonucleotide synthesis and hybridisation properties of oligonucleotides synthesised in situ," Nucleic Acids Research, 20(7):1679-1684 (Apr. 1992).
Mattheakis et al., "An in vitro polysome display system for identifying ligands from very large peptide libraries," Proceedings of the National Academy of Sciences USA, 91(19):9022-9026 (Sep. 1994).
Medynski, "Synthetic peptide combinatorial libraries," Bio/technology (Nature Publishing Company), 12(7):709-710 (Jul. 1994).
Mhawech, "14-3-3 proteins—an update," Cell Research, 15(4):228-236 (Apr. 2005).
Millar et al., "Disruption of two novel genes by a translocation co-segregating with schizophrenia," Human Molecular Genetics, 9(9):1415-1423 (May 2000).
Moore et al., "Measuring transferrin receptor gene expression by NMR imaging." Biochimica et Biophysica Acta (BBA)-Molecular Cell Research, 1402(3):239-249 (Apr. 1998).
Nakahira et al., "Neuronal generation, migration, and differentiation in the mouse hippocampal primoridium as revealed by enhanced green fluorescent protein gene transfer by means of in utero electroporation," Journal of Comparative Neurology, 483(3):329-340 (Mar. 2005).
Nakata et al., "DISC1 splice variants are upregulated in schizophrenia and associated with risk polymorphisms," Proceedings of the National Academy of Sciences USA, 106(37): 15873-15878 (Sep. 2009).
Ohlmeyer et al., "Complex synthetic chemical libraries indexed with molecular tags." Proceedings of the National Academy of Sciences USA, 90(23):10922-10926 (Dec. 1993).
Pease et al., "Light-generated oligonucleotide arrays for rapid DNA sequence analysis," Proceedings of the National Academy of Sciences USA, 91(11):5022-5026 (May 1994).
Ramshaw et al., "Locomotor hyperactivity in 14-3-3ζ KO mice is associated with dopamine transporter dysfunction," Translational Psychiatry, 3(12):e327 (Dec. 2013).

(56) References Cited

OTHER PUBLICATIONS

Rosner el al., "14-3-3 proteins are involved in the regulation of mammalian cell proliferation," Amino Acids, 30(1):105-109 (Feb. 2006).

Salmon et al., "Discovery of biologically active peptides in random libraries: solution-phase testing after staged orthogonal release from resin beads," Proceedings of the National Academy of Sciences USA, 90(24):11708-11712 (Dec. 1993).

Schiff et al., "Further delineation of the 17p13.3 microdeletion involving YWHAE but distal to PAFAH1B1: four additional patients," European Journal of Medical Genetics, 53(5):303-308 (Oct. 2010).

Scott et al., "Searching for peptide ligands with an epitope library," Science, 249(4967):386-390 (Jul. 1990).

Sekiguchi et al:, "Impairment of the tyrosine hydroxylase neuronal network in the orbitofrontal cortex of a genetically modified mouse model of schizophrenia," Brain Research, 1392:47-53 (May 2011).

Şik et al., "Performance of different mouse strains in an object recognition task," Behavioural Brain Research, 147(1-2):49-54 (Dec. 2003).

Smith et al., "Direct mechanical measurements of the elasticity of single DNA molecules by using magnetic beads," Science, 258(5085):1122-1126 (Nov. 1992).

Sofia, "Carbohydrate-based combinatorial libraries," Molecular Diversity, 3:75-94 (1998).

Su et al., "14-3-3Σ regulates B-cell homeostasis through stabilization of FOXO1," Proceedings of the National Academy of Sciences USA, 2Q W 108(4):1555-1560 (Jan. 2011).

Summers et al., "Prenatal zinc treatment at the time of acute ethanol exposure limits spatial memory impairments in mouse offspring," Pediatric Research, 59(1):66-71 (Jan. 2006).

Taurines, Regina et al., "Proteomic research in psychiatry" Journal of Psychopharmacology, Feb. 2010, pp. 1-46.

Taylor et al., "Evolutionary constraints on the Disrupted in Schizophrenia locus," Genomics, 81(1):67-77 (Jan. 2003).

Tietze et al, "Domino reactions for library synthesis of small molecules in combinatorial chemistry," Current Opinion in Chemical Biology, 2(3):363-371 (Jun. 1998).

Toyo-Oka et al., "14-3-3ε is important for neuronal migration by binding to NUDEL: a molecular explanation for Miller-Dieker syndrome," Nature Genetics, 34(3):274-285 (Jul. 2003).

Tzivion, et al.,"14-3-3 proteins: active cofactors in cellular regulation by serine/threonine phosphorylation," Journal of Biological Chemistry, 277(5):3061-3064 (Feb. 2002).

Van Den Buuse et al., "Neuregulin 1 hypomorphic mutant mice: enhanced baseline locomotor activity but normal psychotropic drug-induced hyperlocomotion and prepulse inhibition regulation," International Journal of Neuropsychopharmacology, 12(10):1383-1393 (Nov. 2009).

Walf et al., "The use of the elevated plus maze as an assay of anxiety-related behavior in rodents," Nature Protocols, 2(2):322-328 (Mar. 2007).

Wang, Hong-Sheng et al., "Association Study Between NPY and YWHAH Gene Polymorphisms and Schizophrenia" Acta Genetica Sinica, Dec. 2005, pp. 1235-1240, vol. 32, No. 12—Abstract.

Wedemeyer et al., "Flow cytometric quantification of competitive reverse transcription-PCR products," Clinical Chemistry, 48(9):1398-1405 (Sep. 2002).

Weissleder et al., "In vivo magnetic resonance imaging of transgene expression," Nature Medicine, 6(3):351-354 (Mar. 2000).

Winters et al., "Glutamate receptors in perirhinal cortex mediate encoding, retrieval, and consolidation of object recognition memory," The Journal of Neuroscience, 25(17):4243-4251 (Apr. 2005).

Wong et al., "Genetic and post-mortem mRNA analysis of the 14-3-3 genes that encode phosphoserine/threonine-binding regulatory proteins in schizophrenia and bipolar disorder," Schizophrenia Research, 78(2-3):137-146 (Oct. 2005).

Xing et al., "14-3-3 proteins block apoptosis and differentially regulate MAPK cascades," The EMBO Journal, 19(3):349-358 (Feb. 2000).

Yaffe, "How do 14-3-3 proteins work?—Gatekeeper phosphorylation and the molecular anvil hypothesis," FEBS Letters, 513(1):53-57 (Feb. 2002).

* cited by examiner

SCREENING METHOD

CROSS REFERENCE TO RELATED APPLICATIONS

This application is a U.S. National Phase Application of PCT International Application Number PCT/AU2012/001141, filed on Sep. 21, 2012, designating the United States of America and published in the English language, which is an International Application of and claims the benefit of priority to Australian Patent Application No. 2011903906. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 35 U.S.C. §1.52(e). The name of the ASCII text file for the Sequence Listing is SeqList-WMRK9-001APC.txt, the date of creation of the ASCII text file is Mar. 20, 2014, and the size of the ASCII text file is 6 KB.

FIELD OF THE INVENTION

The present invention provides a method of screening a mammal for the onset or predisposition to the onset of a neuropsychiatric disorder. More particularly, the present invention provides a method of screening a mammal for the onset or predisposition to the onset of schizophrenia by screening for a decrease in the functional level of protein 14-3-3ζ. In a related aspect, the present invention also provides a means of monitoring a patient diagnosed with a neuropsychiatric disorder, such as schizophrenia, by screening for changes to functional levels of protein 14-3-3ζ. This may be useful, for example, in the context of evaluating the effectiveness of a prophylactic or therapeutic treatment regime or otherwise monitoring the impact of physiological or metabolic changes which may occur in a patient. The method of the present invention is useful in a wide range of applications including, inter alia, providing a means of identifying mammals susceptible to the onset of a neuropsychiatric condition, such as a condition characterised by one or more symptoms of schizophrenia, thereby enabling the implementation of prophylactic or early therapeutic intervention in an effort to either minimise or prevent the onset of the condition. It also provides a means of confirming diagnoses which would otherwise be based solely on an assessment of positive and negative symptoms.

In a related aspect, the present invention also provides an animal model which is useful, inter alia, for screening for or evaluating agents for use in treating a neuropsychiatric condition.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

Schizophrenia is one of the most disabling and emotionally devastating illnesses known to man. Unfortunately, because it has been misunderstood for so long, it has received relatively little attention and its victims have been undeservingly stigmatized. Schizophrenia is, in fact, a fairly common disorder. It affects both sexes equally and strikes about 1% of the population worldwide. Another 2-3% have schizotypal personality disorder, a milder form of the disease. Because of its prevalence and severity, schizophrenia has been studied extensively in an effort to develop better criteria for diagnosing the illness.

Schizophrenia is characterized by a constellation of distinctive and predictable symptoms. The symptoms that are most commonly associated with the disease are called positive symptoms, that denote the presence of grossly abnormal behaviour. These include thought disorder (speech which is difficult to follow or jumping from one subject to another with no logical connection), delusions (false beliefs of persecution, guilt, grandeur or being under outside control) and hallucinations (visual or auditory). Thought disorder is the diminished ability to think clearly and logically. Often it is manifested by disconnected and nonsensical language that renders the person with schizophrenia incapable of participating in conversation, contributing to his alienation from his family, friends and society. Delusions are common among individuals with schizophrenia. An affected person may believe that he is being conspired against (called "paranoid delusion"). "Broadcasting" describes a type of delusion in which the individual with this illness believes that his thoughts can be heard by others. Hallucinations can be heard, seen or even felt. Most often they take the form of voices heard only by the afflicted person. Such voices may describe the person's actions, warn him of danger or tell him what to do. At times the individual may hear several voices carrying on a conversation. Less obvious than the above "positive symptoms" and "thought disorder" but equally serious are the deficit or negative symptoms that represent the absence of normal behaviour. These include flat or blunted affect (i.e. lack of emotional expression), apathy, social withdrawal and lack of insight.

The onset of schizophrenia usually occurs during adolescence or early adulthood, although it has been known to develop in older people. Onset may be rapid with acute symptoms developing over several weeks, or it may be slow developing over months or even years. While schizophrenia can affect anyone at any point in life, it is somewhat more common in those persons who are genetically predisposed to the disease with the first psychotic episode generally occurring in late adolescence or early adulthood. The probability of developing schizophrenia as the offspring of two parents, neither of whom has the disease, is 1 percent. The probability of developing schizophrenia as the offspring of one parent with the disease is approximately 13 percent. The probability of developing schizophrenia as the offspring of both parents with the disease is approximately 35 percent. This is indicative of the existence of a genetic link.

Three-quarters of persons with schizophrenia develop the disease between 16 and 25 years of age. Onset is uncommon after age 30 and rare after age 40. In the 16-25 year old age group, schizophrenia affects more men than women. In the 25-30 year old group, the incident is higher in women than in men.

In general, the study of any illness requires that there should be good criteria for diagnosis. In fact, diagnosis should ultimately be based on causes i.e., on whether an illness results from a genetic defect, a viral or bacterial infection, toxins or stress. Unfortunately, the causes of most psychiatric illnesses are unknown and therefore these disorders are still grouped according to which of the four major mental faculties are affected:

(i) disorders of thinking and cognition
(ii) disorders of mood
(iii) disorders of social behaviour; and
(iv) disorders of learning, memory and intelligence.

Accordingly, since so little is known of the biological causes of these conditions, there is an ongoing need to elucidate the mechanisms by which these diseases are induced and progress.

The 14-3-3 proteins constitute a family of highly conserved regulatory molecules expressed abundantly throughout development and in adult tissue. These proteins comprise seven distinct isoforms (β, ζ, ε, γ, η, τ, σ), that bind a multitude of functionally diverse signalling molecules to control cell cycle regulation, proliferation, migration, differentiation and apoptosis (Berg et al. *Nat Rev Neurosci* 2003; 4(9):752-762; Fu et al. *Annu Rev Pharmacol Toxicol* 2000; 40:617-647; Toyo-oka et al. *Nat Genet* 2003 July; 34(3): 274-285; Aitken A. *Semin Cancer Biol* 2006; 16(3): 162-172; Rosner et al. *Amino Acids* 2006; 30(1):105-109).

To date, the role, if any, of the protein 14-3-3 family of molecules in schizophrenia has remained elusive. Some research has focussed, albeit so far inconclusively, on identifying single nuclear polymorphisms associated with a predisposition to developing a neuropsychiatric condition such as schizophrenia. Studies aimed at investigating changes to levels of protein 14-3-3 isoforms, irrespective of whether or not those molecules are mutated, have tended to focus on changes to the levels of the eta and theta isoforms, although to date there has not been any conclusive-evidence that they are reliable markers of the onset of a neuropsychiatric condition. In relation to other of the protein 14-3-3 isoforms, such as beta and zeta, Wong et al. (2005) found no change to expression levels in schizophrenia and bipolar disorders. Middleton et al. (2005) went further and stated that these particular isoforms are not likely to be directly related to a genetic risk for developing schizophrenia and that neither marker provides a strong association with schizophrenia.

Nevertheless, and contrary to these findings, in work leading up to the present invention it has been determined that a reduction in the functional level of protein 14-3-3ζ is associated with the onset of or predisposition to the onset of a neuropsychiatric disorder, such as a condition which is characterised by one or more symptoms of schizophrenia. Still further, it has also been determined that a reduction in the level of protein 14-3-3ζ/DISC1 complex formation is similarly diagnostic. These findings have now facilitated the design of methodology to routinely and accurately screen individuals to confirm the onset of, or a predisposition to the development of, a neuropsychiatric disorder.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

The subject specification contains nucleotide sequence information prepared using the programme PatentIn Version 3.5, presented herein after the bibliography. Each nucleotide sequence is identified in the sequence listing by the numeric indicator <210> followed by the sequence identifier (e.g. <210>1, <210>2, etc). The length, type of sequence (DNA; RNA, etc.) and source organism for each nucleotide sequence are indicated by information provided in the numeric indicator fields <211>, <212> and <213>, respectively. Nucleotide sequences referred to in the specification are identified by the indicator SEQ ID NO: followed by the sequence identifier (e.g. SEQ ID NO:1, SEQ ID NO:2, etc.). The sequence identifier referred to in the specification correlates to the information provided in numeric indicator field <400> in the sequence listing, which is followed by the sequence identifier (e.g. <400>1, <400>2, etc.). That is, SEQ ID NO:1 as detailed in the specification correlates to the sequence indicated as <400>1 in the sequence listing.

One aspect of the present invention is directed to a method of screening a mammal for the onset or predisposition to the onset of a neuropsychiatric condition said method comprising determining the functional level of protein 14-3-3ζ in a biological sample derived from said mammal wherein a lower level of said protein 14-3-3ζ relative to control levels is indicative of the onset or predisposition to the onset of said condition.

In another aspect there is provided a method of screening a human for the onset or predisposition to the onset of a neuropsychiatric condition said method comprising determining the functional level of protein 14-3-3ζ in a biological sample derived from said human wherein a lower level of said protein 14-3-3ζ relative to control levels is indicative of the onset or predisposition to the onset of said condition.

In still another aspect is therefore provided a method of screening a human for the onset or predisposition to the onset of a condition characterised by one or more symptoms characteristic of schizophrenia said method comprising determining the functional level of protein 14-3-3ζ in a biological sample derived from said human wherein a lower level of said protein 14-3-3ζ relative to control levels is indicative of the onset or predisposition to the onset of said condition.

In yet another aspect there is provided a method of screening a human for the onset or predisposition to the onset of schizophrenia, said method comprising determining the functional level of protein 14-3-3ζ in a biological sample derived from said human wherein a lower level of said protein 14-3-3ζ relative to control levels is indicative of the onset or predisposition to the onset of said schizophrenia.

The present invention therefore provides a method of diagnosing the onset of a neuropsychiatric condition in a human presenting with one or more positive or negative symptoms or thought disorder said method comprising determining the functional level of protein 14-3-3ζ in a biological sample from said human wherein a lower level of said protein 14-3-3ζ relative to control levels is indicative of the onset of said condition.

In still yet another aspect the present invention is directed to a method of screening a mammal for the onset or predisposition to the onset of a neuropsychiatric condition said method comprising determining the level of expression of the gene encoding protein 14-3-3ζ in a biological sample derived from said mammal wherein a lower level of expression relative to control levels is indicative of the onset or predisposition to the onset of said condition.

In a further aspect the present invention is directed to a method of screening a mammal for the onset or predisposition to the onset of a neuropsychiatric condition said method comprising determining the level of protein 14-3-3ζ/DISC1 complex formation in a biological sample derived from said mammal wherein a lower level of complex formation relative to control levels is indicative of the onset or predisposition to the onset of, said condition.

Still another further aspect of the present invention is directed to a method of monitoring the progression of a neuropsychiatric condition in a mammal diagnosed with the onset of said condition said method comprising determining the functional level of protein 14-3-3ζ in a biological sample derived from said mammal wherein an equal or lower level of protein 14-3-3ζ relative to a level previously obtained for that mammal is indicative of a poor prognosis and a higher level of protein 14-3-3ζ relative to a level previously obtained for that mammal is indicative of an improved prognosis.

Yet another aspect of the present invention is directed to a method of monitoring a patient determined to be predisposed to the onset of a neuropsychiatric condition said method comprising determining the functional level of protein 14-3-3ζ in a biological sample derived from said mammal wherein an equal or lower level of protein 14-3-3ζ relative to a level previously obtained for that mammal is indicative of an improved prognosis.

Another aspect of the present invention is directed to a non-human mammal deficient in functional protein 14-3-3ζ in which a gene encoding protein 14-3-3ζ has been detected.

Yet another aspect of the present invention is directed to a method of screening for an agent which mimics protein 14-3-3ζ functionality or 14-3-3ζ/DISC1 complex formation or otherwise improves the symptoms of a schizophrenic phenotype, said method comprising administering to a 14-3-3ζ knockout non-human animal a putative modulation agent and screening for altered phenotype.

Figure 1:
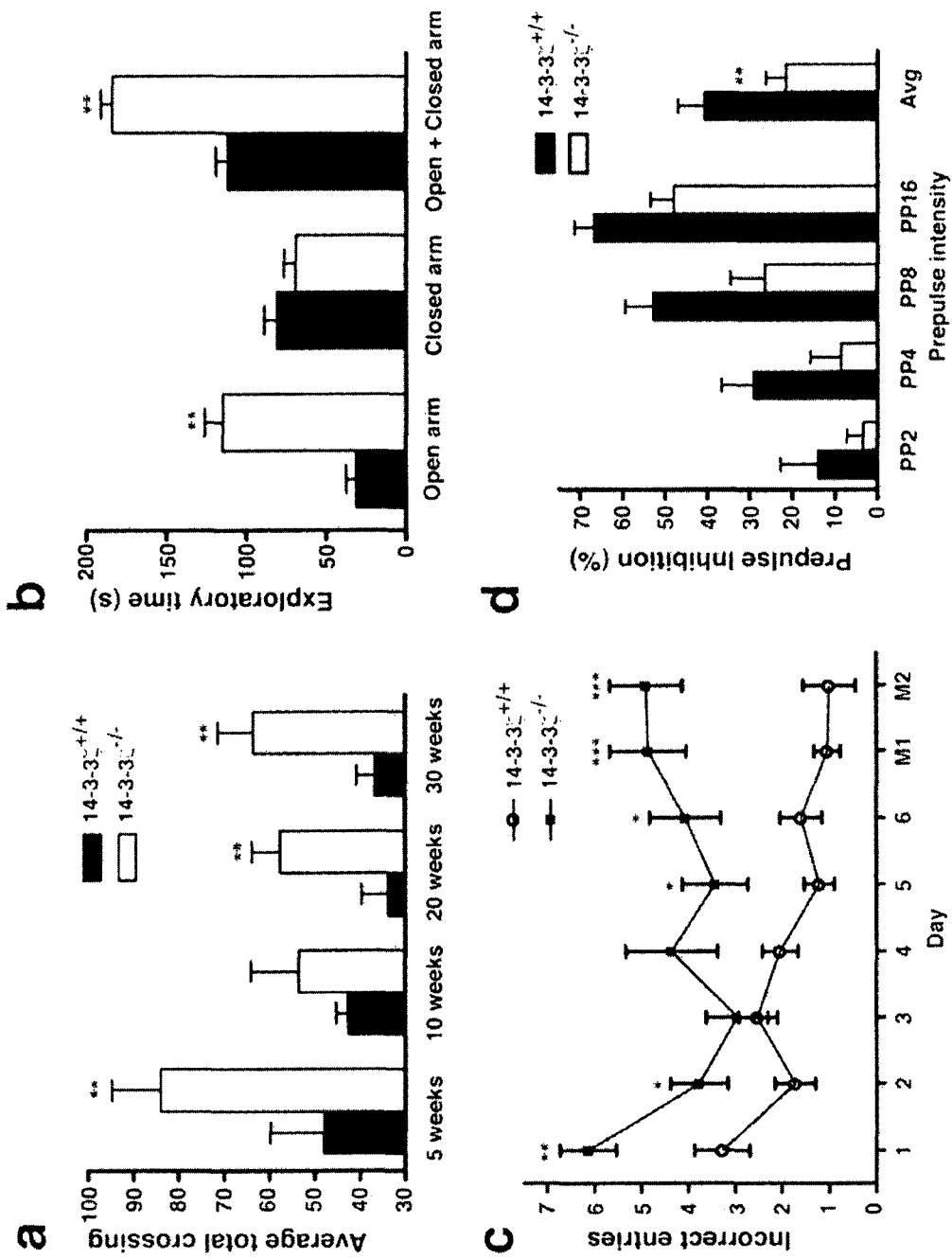
FIG. 1: 14-3-3ζ-deficient mice demonstrate abnormal cognitive and behavioural traits. (a) 14-3-3ζ$^{062-/-}$ mice (open bars; n=11) have greater exploratory behaviour at 5-30 weeks of age than 14-3-3ζ$^{062+/+}$ littermates (filled bars; n—11) in an open field test. (b) 14-3-3ζ$^{062-/-}$ mice (open bars; n=12) spend more time than 14-3-3ζ$^{062+/+}$ mice (filled bars; n=12) in the open arm in an elevated plus maze. (c) 14-3-3ζ$^{062-/-}$ mice (open circles; n=12) have lower capacity than 14-3-3ζ$^{062+/+}$ mice (closed squares; n=12) for both spatial learning (Day 1-6) and memory (M1 and M2) in a cross maze escape task test. (d) Compared to 14-3-3ζ$^{062+/+}$ mice (filled bars; n=11) the 14-3-3ζ$^{062-/-}$ mice (open bars; n=11) have reduced PPI with a prepulse (PP) of 2, 4, 8 and 16 dB over the 70 dB baseline and an inter-stimulus interval of 100 msec. The average (Avg) of data from all PP intensities is also shown. Data from male and female mice is pooled in all graphs. Error bars are presented as mean±SEM. *, p<0.05; , p<0.01; *, p<0.001.

(A) Dendritic spines are reduced in the granular neurons of the dentate gyrus (DG) in 14-3-3ζ$^{062-/-}$ mice (n=3, 20 dendrites counted from each animal) compared to 14-3-3ζ$^{062+/+}$ mice (n+4, 20 dendrites counted from each animal). (B) Dendritic spines are also reduced in the pyramidal neurons of the cornu ammonis (CA) in 14-3-3ζ$^{062-/-}$ mice (n=3, 20 dendrites counted from each animal) compared to 14-3-3ζ$^{062+/+}$ mice (n+4, 20 dendrites counted from each animal). Left panels show representative images of spines in a 14-3-3ζ$^{062-/-}$ and 14-3-3ζ$^{062+/+}$ DG dendrites or CA dendrites. Right panels indicate quantification with relevant p values. Note, scoring of spine numbers was completed blind for all animals.

DETAILED DESCRIPTION OF THE INVENTION

The present invention is predicated, in part, on the determination that a reduction in the functional level of protein 14-3-3ζ, such as in the context of absolute levels of protein 14-3-3ζ or levels of protein 14-3-3ζ/DISC1 complex formation, is indicative of the onset or predisposition to the onset of a neuropsychiatric condition, such as schizophrenia or related condition. This finding has therefore facilitated the development of a simple yet highly useful test for assessing susceptibility to or diagnosing onset of a neuropsychiatric condition: Also facilitated is the generation of genetically modified animals which do not express protein 14-3-3ζ and methods for their use, such as in the context of developing or testing known or new therapeutic or prophylactic treatment regimes or screening for modulatory agents which may be useful in this regard.

Accordingly, one aspect of the present invention is directed to a method of screening a mammal for the onset or predisposition to the onset of a neuropsychiatric condition said method comprising determining the functional level of protein 14-3-3ζ in a biological sample derived from said mammal wherein a lower level of said protein 14-3-3ζ relative to control levels is indicative of the onset or predisposition to the onset of said condition.

Without limiting the present invention to any one theory or mode of action, the 14-3-3 proteins are a conserved family of dimeric phospho-serine binding proteins that interact and modulate the functions of multiple cellular proteins and in so doing regulate many signalling pathways (Tzivion and Avruch 2002, *J. Biol. Chem.* 277:3061-64; Fu et al. 2000, *Ann. Rev. Pharma. Tox.* 40:617-47). The 14-3-3 proteins are composed of two 30 kDa monomer units that are each capable of binding a phospho-serine motif via an amphipathic groove. Dimers of 14-3-3 are formed by the N-terminal a helices, with helix 1 of one monomer interacting with helices 3 and 4 of another. Functionally, 14-3-3 proteins perform multiple roles in regulating cellular protein activities and importantly, these functions of 14-3-3 are dependent on its dimeric structure (Xing et al. 2000, supra; Yaffe 2002, *FEBS Letts.* 513:53-57). The 14-3-3 proteins are a highly conserved family of seven phospho-serine binding proteins. The seven isoforms are the β, ε, γ, η, σ, τ and ζ (NCBI Ref. Sequence Number NM_003406.3; SEQ ID NO:1) forms.

Reference to "protein 14-3-3ζ" should be understood to include reference to all forms of protein 14-3-3ζ including functional allelic or polymorphic variants. Reference to "variants" should be understood to extend to functional mutants. Reference to "homologues" should be understood as a reference to 14-3-3 proteins from species other than human. Reference to a "functional" 14-3-3 protein should be understood as a reference to a molecule which can undergo DISC1 complex formation and thereby facilitate ongoing signalling via the DISC1 regulated network. It should be understood that "protein 14-3-3ζ" is also interchangeably referred to as "14-3-3ζ" in this specification. Both terms should be understood as a reference to the same molecule. In one embodiment, said protein 14-3-3ζ is human 14-3-3ζ.

According to this embodiment there is provided a method of screening a human for the onset or predisposition to the onset of a neuropsychiatric condition said method comprising determining the functional level of protein 14-3-3ζ in a biological sample derived from said human wherein a lower level of said protein 14-3-3ζ relative to control levels is indicative of the onset or predisposition to the onset of said condition.

Reference to a "neuropsychiatric condition" should be understood as a reference to a condition characterised by neurologically based cognitive, emotional and behavioural disturbances. Examples of such conditions include, inter alia, a condition characterised by one or more symptoms of schizophrenia, schizophrenia, schizotypal personality disorder, psychosis, bipolar disorder, manic depression, affective disorder, or schizophreniform or schizoaffective disorders, psychotic depression, autism, drug induced psychosis, delirium, alcohol withdrawal syndrome or dementia induced psychosis.

In one embodiment, said neuropsychiatric condition is a condition which is characterised by one or more symptoms of schizophrenia.

According to this embodiment there is therefore provided a method of screening a human for the onset or predisposition to the onset of a condition characterised by one or more symptoms characteristic of schizophrenia said method comprising determining the functional level of protein 14-3-3ζ in a biological sample derived from said human wherein a lower level of said protein 14-3-3ζ relative to control levels is indicative of the onset or predisposition to the onset of said condition.

Reference to "symptoms characteristic of schizophrenia" should be understood as a reference to any one or more symptoms which may occur in an individual suffering from schizophrenia. These symptoms may be evident throughout the disease course or they may be evident only transiently or periodically. For example, the hallucinations associated with schizophrenia usually occur in periodic episodes while the characteristic social withdrawal may exhibit an ongoing manifestation. It should also be understood that the subject symptoms may not necessarily be exhibited by all individuals suffering from schizophrenia. For example, some individuals may suffer from auditory hallucinations only while others may suffer only from visual hallucinations. However, for the purpose of the present invention, any such symptoms, irrespective of how many or few schizophrenia patients ever actually exhibit the given symptom, are encompassed by this definition. Without limiting the present invention to any one theory or mode of action, the symptoms that are most commonly associated with the disease are called positive symptoms (which denote the presence of grossly abnormal behaviour), thought disorder and negative symptoms. Thought disorder and positive symptoms include speech which is difficult to follow or jumping from one subject to another with no logical connection, delusions (false beliefs of persecution, guilt, grandeur or being under outside control) and hallucinations (visual or auditory). Thought disorder is the diminished ability to think clearly and logically. Often it is manifested by disconnected and nonsensical language that renders the person with schizophrenia incapable of participating in conversation, contributing to alienation from family, friends and society. Delusions are common among individuals with schizophrenia. An affected person may believe that he or she is being conspired against (called "paranoid delusion"). "Broadcasting" describes a type of delusion in which the individual with this illness believes that their thoughts can be heard by others. Hallucinations can be heard, seen or even felt. Most often they take the form of voices heard only by the afflicted person. Such voices may describe the person's actions, warn of danger or tell him what to do. At times the individual may hear several voices carrying on a conversation. Less obvious than the "positive symptoms" but equally serious are the deficit or negative symptoms that represent the absence of normal behaviour. These include flat or blunted affect (i.e. lack of emotional expression), apathy, social withdrawal and lack of insight. Both the positive symptoms and the negative symptoms should be understood to fall within the definition of "symptoms characteristic of schizophrenia".

In addition to the fact that there may be significant variation between schizophrenia patients in terms of which symptoms they exhibit, it should also be understood that there are other neuropsychiatric conditions which are also characterised by one or more of these symptoms. Hallucinations, for example, are also commonly observed in patients with bipolar disorder, psychotic depression, delirium and dementia induced psychosis, for example. Accordingly, reference to a condition characterised by one or more symptoms characteristic of schizophrenia should be understood as a reference to any neuropsychiatric condition which is characterised by the presence of one or more of these symptoms. In one embodiment, said condition is schizophrenia.

According to this embodiment there is provided a method of screening a human for the onset or predisposition to the onset of schizophrenia, said method comprising determining the functional level of protein 14-3-3ζ in a biological sample derived from said human wherein a lower level of said protein 14-3-3ζ relative to control levels is indicative of the onset or predisposition to the onset of said schizophrenia.

The term "mammal" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably, the mammal is a human or a laboratory test animal. Even more preferably, the mammal is a human.

Individuals exhibiting protein 14-3-3ζ levels lower than the normal range are generally regarded as having undergone the onset of the subject condition, as opposed to a predisposition to its onset, where there is also evidence of the onset one or more positive or negative symptoms, as hereinbefore described. It would be appreciated that one of the limitations of diagnosing neuropsychiatric conditions such as schizophrenia has been that in the early stages of the condition, the symptoms which are observed are non-specific and can often be attributed to non-neuropsychiatric causes. This makes diagnosis extremely difficult, particularly when the stigma associated with having a condition such as schizophrenia can lead to a reluctance by health professionals or patients' families to acknowledge such a diagnosis in the absence of absolute certainty in this regard. Where an incorrect diagnosis is made, the consequences can be serious since a therapeutic treatment regime may be designed which will not, in fact, be effective or may even be detrimental. Accordingly, the method of the present invention now provides a means of obtaining a conclusive diagnosis in these types of situations since the observance of the onset of symptoms characteristic of a neuropsychiatric condition can now be assessed together with a biochemical readout in order to provide a firm diagnosis.

The present invention therefore provides a method of diagnosing the onset of a neuropsychiatric condition in a human presenting with one or more positive or negative symptoms or thought disorder said method comprising determining the functional level of protein 14-3-3ζ in a biological sample from said human wherein a lower level of said protein 14-3-3ζ relative to control levels is indicative of the onset of said condition.

In one embodiment, said condition is a condition characterised by one or more symptoms of schizophrenia.

In another embodiment, said condition is schizophrenia.

As detailed hereinbefore, the present invention also provides a means of determining whether or not a patient is predisposed to developing a neuropsychiatric condition. In this situation, the individual is typically not yet exhibiting any symptoms of a neuropsychiatric condition. However, due to any one of a number of factors, such as a family history for example, it may be desirable to determine whether that individual is predisposed to the onset of such a condition. This can provide valuable information which may enable lifestyle changes to be made or prophylactic drug treatment regimens to be implemented. Reference to "predisposition" in this regard should therefore be understood as a reference to an increased tendency or susceptibility to the onset of such a condition relative to a normal individual. It does not mean that the individual will necessarily develop the condition, for example if the individual is not exposed to a trigger for the onset of the condition, but merely that under circumstances where the onset of the condition could be triggered, it is more likely that a person predisposed to the condition would develop it than someone who is not. Reference to an individual who is "not predisposed" to the onset of such a condition should be understood to have the converse meaning. Reference to "predisposition" is also intended to describe an individual who exhibits an increased risk of developing a neuropsychiatric condition relative to that of the general population.

The present invention is predicated on the determination that a reduction in the functional level of protein 14-3-3ζ is indicative of the onset or predisposition to the onset of a neuropsychiatric condition. Reference to the "functional level" should be understood as a reference to the biologically effective level of protein 14-3-3ζ rather than its absolute level, per se. That is, the capacity of protein 14-3-3ζ to effect the biological pathways hereinafter described is the relevant issue, this being impacted upon by measurable factors other than just absolute levels of protein 14-3-3ζ.

Without limiting the present invention to any one theory or mode of action, 14-3-3ζ binds to phosphorylated Ndel1, maintains phosphorylation of Ndel1 and thereby promotes Ndel1 binding to LIS1 and cytoplasmic dyne in heavy chain that regulate nuclear movement. However, it has also now been determined that protein 14-3-3ζ interacts with the tripartite DISC1/Ndel1/LIS1-complex to promote kinesin motor binding and relocation of Ndel1/LIS1 to growing axons. Still further, this preferentially occurs in an isoform-specific manner, with the 14-3-3ζ/DISC1 complex formation and signalling preferentially occurring in the context of the 75 kDa isoform of DISC1 rather than the 100 kDa isoform. These findings are in contrast to the previous findings which demonstrated that Ndel1 in fact interacted with the 100 kDa isoform of DISC1.

The DISC1 protein is encoded by the DISC1 gene in humans (Millar et al. 2000, *Hum. Mol. Genet.* 9(9): 1415-23). In coordination with a wide array of interacting partners, DISC1 has been shown to participate in the regulation of cell proliferation, differentiation, migration, neuronal axon and dendrite outgrowth, mitochondrial transport, fission and/or fusion, and cell-to-cell adhesion. The DISC1 gene is situated at chromosome 1q42.1 and overlaps with DISC2 open reading frame. Multiple DISC1 isoforms have been identified at the RNA level, including a TSNAX-DISC1 transgene splice variant, and at the protein level (Nakata et al. (2009). *Proc Natl Acad Sci USA:* 106(37): 15873-8). Of the isolated RNA isomers, 4 have been confirmed to be translated namely Long form (L), Long variant isoform (Lv), Small isoform (S), and Especially small isoform (Es). Human DISC1 is transcribed as two major splice variants. L form and Lv isoform. The L and Lv transcripts utilize distal and proximal splice sites, respectively, within exon 11. Alternate transcriptional splice variants, encoding different isoforms, have been characterized. DISC1 homologues have been identified in the common chimpanzee, the Rhesus monkey, the house mouse, the brown rat, zebrafish, pufferfish, cattle, and dogs (Taylor et al. (2003) *Genomics* 81(1):67-77).

The protein encoded by this gene, is predicted to contain a coiled coil motif rich C-terminal domain and a N-terminal globular domain (Taylor et al. 2003 supra). The N-terminus contains two putative nuclear localization signals and a serine-phenylalanine-rich motif of unknown significance. The C-terminus contains multiple regions with coiled-coil forming potential and two leucine zippers that May mediate protein-protein interactions. The DISC1 protein has no known enzymatic activity; rather it exerts its effect on multiple proteins through interactions to modulate their functional states and biological activities in time and space (Bradshaw and Porteous (2010 Dec. 31). "DISC1-binding proteins in neural development, signalling and schizophrenia.". *Neuropharmacology*).

Reference to "DISC1" should be understood to have a corresponding meaning to that provided in relation to "protein 14-3-3ζ".

Still without limiting the present invention in any way, a reduction in protein 14-3-3ζ functional levels, in the context of a schizophrenia mouse model, induced behavioural and cognitive defects characteristic of schizophrenia. These deficiencies were noticed as an increase in locomotor function, inability to recognise novel objects, reduced anxiety to an open environment, severely reduced capacity to learn or remember and abnormal sensorimotor gating. Anatomical disturbances of neurons within the hippocampus were also identified and are postulated to arise from aberrant neuronal migration. Also identified were specific axonal navigation defects and abnormal synaptic connectivity of hippocampal mossy fibres, this being consistent with schizophrenia being a disorder of the synapse. More specifically, laminar organisation of the hippocampus was disrupted where 14-3-3ζ functionality was adversely impacted upon. This defect arose primarily from aberrant migration of hippocampal neurons from the subventricular zone to their usual resting place in the stratum pyramidale. The 14-3-3ζ/DISC1 axis is therefore a central biological pathway in the pathophysiology of schizophrenia and the observed anatomical defects are consistent with the fact that the cognitive defects associated with schizophrenia arise from both neurodevelopmental deficiencies and disturbances of the synapse.

In terms of assessing the "biologically effective level" of protein 14-3-3ζ functionality, it should be understood that this can be assessed not only in terms of absolute levels of protein 14-3-3ζ, but also at the level of protein 14-3-3ζ/DISC1 complex formation since it is actually the formation of these complexes which underpins the requisite neurological development. Defects in absolute levels of protein 14-3-3ζ will impact on this complex formation but so too will other structural or functional defects in either the protein 14-3-3ζ molecule or the DISC1 molecule since these lead to an inability for effective complex formation to occur. Without complex formation, the downstream signalling events which are induced by this complex cannot occur. Accordingly, one can therefore screen for both defects in protein 14-3-3ζ expression and defects of other types which may not necessarily impact on protein 14-3-3ζ levels but which nevertheless adversely impact on the ability of 14-3-3ζ to form functional complexes with DISC1. For example, one can screen for:

(i) a decrease in the protein 14-3-3ζ translation product level;

(ii) a decrease in the protein 14-3-3ζ transcription product level (for example, primary RNA or mRNA);

(iii) changes to the chromatin proteins with which the 14-3-3 gene is associated, for example the presence of histone H3 methylated on lysine at amino acid position number 9 or 27 (repressive modifications) or changes to the DNA itself which act to downregulate expression, such as changes to the methylation of the DNA;

(iv) a reduction in the ability of protein 14-3-3ζ and DISC1 to form complexes.

In accordance with this embodiment, the present invention is directed to a method of screening a mammal for the onset or predisposition to the onset of a neuropsychiatric condition said method comprising determining the level of expression of the gene encoding protein 14-3-3ζ in a biological sample derived from said mammal wherein a lower level of expression relative to control levels is indicative of the onset or predisposition to the onset of said condition.

It should be understood that reference to the "expression" of the protein 14-3-3ζ gene is a reference to assessing the level of either the transcription product encoding this particular protein 14-3-3 isoform (e.g. mRNA) or the translation protein (i.e. the protein) itself.

In another embodiment, said level of expression is mRNA expression.

In yet another embodiment, said level of expression is protein expression.

In still another embodiment, said level of expression is assessed by screening for changes to genomic DNA, such as changes to DNA methylation, in particular hypermethylation.

In yet still another embodiment, said level of expression is assessed by screening for changes to the chromatin protein with which said gene is associated.

In a further embodiment the present invention is directed to a method of screening a mammal for the onset or predisposition to the onset of a neuropsychiatric condition said method comprising determining the level of protein 14-3-3ζ/DISC1 complex formation in a biological sample derived from said mammal wherein a lower level of complex formation relative to control levels is indicative of the onset or predisposition to the onset of said condition.

In one embodiment, said complex is a complex between protein 14-3-3ζ and the 75 kDa DISC1 isoform.

It should be understood by the person of skill in the art that reference to the "protein 14-3-3ζ/DISC1 complex" is a reference to a complex comprising both protein 14-3-3ζ and DISC1 but not necessarily only those two molecules. That is, the complex may include other molecules, such as Ndel1 and LIS1. It should also be understood that the 14-3-3ζ protein may not necessarily interact directly with or exclusively to DISC1. That is, it may also interact with Ndel1 and/or LIS1.

The method of the present invention is predicated on the analysis of the level of protein 14-3-3ζ expression in a biological sample relative to a control level of this marker. The "control level" may be either a "normal level", which is the level of protein 14-3-3ζ expression in a corresponding sample taken from an individual who is not suffering from the subject neuropsychiatric condition, or it may be a sample harvested at an earlier point in time from the patient in issue. The latter situation is relevant where the method of the invention is used to monitor a patient over a period of time, for example to assess the effectiveness of a therapeutic or prophylactic treatment regime. This is discussed in more detail hereafter. It should also be understood that the subject protein 14-3-3ζ may be assessed or monitored by either quantitative or qualitative readouts.

The normal level may be determined using a biological sample corresponding to the sample being analysed but which has been isolated from an individual who has not developed the condition nor is predisposed to developing the condition. However, it would be appreciated that it is likely to be most convenient to analyse the test results relative to a standard result which reflects individual or collective results obtained from healthy individuals. This latter form of analysis is in fact the preferred method of analysis since it enables the design of kits which require the collection and analysis of a single biological sample, being a test sample of interest. The standard results which provide the normal level may be calculated by arty suitable means which would be well known to the person of skill in the art. For example, a population of normal tissues can be assessed in terms of the level of 14-3-3ζ thereby providing a standard value or range of values against which all future test samples are analysed. It should also be understood that the normal level may be determined from the subjects of a specific cohort and for use with respect to test samples derived from that cohort. Accordingly, there may be determined a number of standard values or ranges which correspond to cohorts which differ in respect of characteristics such as age, gender, ethnicity or health status. Said "normal level" may be a discrete level or a range of levels.

Although the preferred method is to detect a decrease in protein 14-3-3ζ levels in order to diagnose the onset of or predisposition to the onset of the subject condition, the detection of increases in protein 14-3-3ζ levels may be desired under certain circumstances. For example, one may seek to monitor an individual for changes in disease state or for prognostic implications in relation to the development or onset of acute episodes of psychosis, such as during the course of prophylactic or therapeutic treatment of the patients. Alternatively, patients presenting with symptoms of schizophrenia, for example, or a genetic or environmental predisposition to the development of such a condition may be monitored. It should be understood that in accordance with this aspect of the present invention, 14-3-3ζ functional protein levels will likely be assessed relative to one or more previously obtained results, as hereinbefore described.

The method of the present invention is therefore useful as a one off test, as an on-going monitor of those individuals thought to be at risk of the development of such a condition or as a monitor of the effectiveness of therapeutic or prophylactic treatment regimes directed to inhibiting or otherwise slowing the onset or progression of such a condition. Accordingly, the method of the present invention should be understood to extend to monitoring for increases or decreases in protein 14-3-3ζ levels in an individual relative to a normal level (as hereinbefore defined) or relative to one or more earlier levels determined from said individual.

Accordingly, another aspect of the present invention is directed to a method of monitoring the progression of a neuropsychiatric condition in a mammal diagnosed with the onset of said condition said method comprising determining the functional level of protein 14-3-3ζ in a biological sample derived from said mammal wherein an equal or lower level of protein 14-3-3ζ relative to a level previously obtained for that mammal is indicative of a poor prognosis and a higher level of protein 14-3-3ζ relative to a level previously obtained for that mammal is indicative of an improved prognosis.

Yet another aspect of the present invention is directed to a method of monitoring a patient determined to be predisposed to the onset of a neuropsychiatric condition said method comprising determining the functional level of protein 14-3-3ζ in a biological sample derived from said mammal wherein an equal or lower level of protein 14-3-3ζ relative to a level previously obtained for that mammal is indicative of an improved prognosis.

In one embodiment, said condition is characterised by one or more symptoms of schizophrenia.

In another embodiment, said condition is schizophrenia.

In still another embodiment, said mammal is a human.

In another embodiment, said level of expression is mRNA expression.

In yet another embodiment, said level of expression is protein expression.

In still another embodiment, said level of expression is assessed by screening for changes to genomic DNA, such as changes to DNA methylation, in particular hypermethylation.

In yet still another embodiment, said level of expression is assessed by screening for changes to the chromatin protein with which said gene is associated.

In still yet another embodiment said functional level is the level of protein 14-3-3ζ/DISC1 complex formation, more particularly 14-3-3ζ/75 kDa DISC1 isoform complex formation.

Without limiting the present invention in any way, the method of the present invention is particularly useful since protein 14-3-3ζ expression is detectable outside the brain. Most previously identified markers of schizophrenia have taken the form of mutations present in the transcription product of genes expressed only in the brain. From a diagnostic perspective, this is not desirable since the prospect of harvesting brain tissue for testing, particularly routine testing, is unpalatable to the patient and potentially open to the development of serious complications, such as infection, due to its highly invasive nature. The present findings, however, have enabled the use of other biological sources, including the cerebrospinal fluid, peripheral blood and adult derived neural stem cells from tissues such as dental pulp, hair follicle and nasal pit. The development of this test has now rendered possible significantly simpler and routine testing of individuals for schizophrenia.

Reference to a "biological sample" should therefore be understood as a reference to any sample of biological material derived from an animal such as, but not limited to, cellular material, tissue biopsy specimens or bodily fluid (e.g. cerebrospinal fluid or blood). The biological sample which is tested according to the method of the present invention may be tested directly or may require some form of treatment prior to testing. For example, a biopsy sample may require homogenisation prior to testing or it may require sectioning for in snit testing. Further, to the extent that the biological sample is not in liquid form, (if such form is required for testing) it may require the addition of a reagent, such as a buffer, to mobilise the sample. Preferably, said biological sample is a sample of peripheral blood lymphocytes or adult derived neural stem cells.

To the extent that the target molecule is present in a biological sample, the biological sample may be directly tested or else all or some of the nucleic acid material or protein present in the biological sample may be isolated prior to testing. In yet another example, the sample may be partially purified or otherwise enriched prior to analysis. For example, to the extent that a biological sample comprises a very diverse cell population, it may be desirable to select out a sub-population of particular interest (e.g. CNS cells) if mRNA is the subject of analysis. It is within the scope of the present invention for the target nucleic acid or protein molecule to be pre-treated prior to testing, for example inactivation of live virus or being run on a gel. It should also be understood that the biological sample may be freshly harvested or it may have been stored (for example by freezing) prior to testing or otherwise treated prior to testing (such as by undergoing culturing).

The choice of what type of sample is most suitable for testing in accordance with the method disclosed herein will be dependent on the nature of the situation.

As detailed hereinbefore reference to "expression" should be understood as a reference to the transcription and/or translation in a nucleic acid molecule. Reference to "RNA" should be understood to encompass reference to any form of RNA, such as primary RNA or mRNA. Without limiting the present invention in any way, the modulation of gene transcription leading to increased or decreased RNA synthesis will also correlate with the translation of these RNA transcripts (such as mRNA) to a protein product. Accordingly, the present invention also extends to detection methodology which is directed to screening for modulated levels or patterns of the protein 14-3-3ζ products as an indicator of the neoplastic state of a cell or cellular population. Although one method is to screen for mRNA transcripts and/or the corresponding protein product, it should be understood that the present invention is not limited in this regard and extends to screening for any other form of expression product such as, for example, a primary RNA transcript.

In terms of screening for the downregulation of expression of protein 14-3-3ζ it would also be well known to the person of skill in the art that changes which are detectable at the DNA level are indicative of changes to gene expression activity and therefore changes to expression product levels. Such changes include but are not limited to, changes to DNA methylation. Accordingly, reference herein to "screening the level of expression" and comparison of these "levels of expression" to control "levels of expression" should be understood as a reference to assessing DNA factors which are related to transcription, such as gene/DNA methylation patterns.

It would also be known to a person skilled in the art that changes in the structure of chromatin are indicative of changes in gene expression. Silencing of gene expression is often associated with modification of chromatin proteins, methylation of lysines at either or both positions 9 and 27 of histone H3 being well studied examples, while active chromatin is marked by acetylation of lysine 9 of histone H3. Thus association of gene sequences with chromatin carrying repressive or active modifications can be used to make an assessment of the expression level of a gene.

Reference to "nucleic acid molecule" should be understood as a reference to both deoxyribonucleic acid molecules and ribonucleic acid molecules and fragments thereof. The present invention therefore extends to both directly screening for mRNA levels in a biological sample or screening for the complementary cDNA which has been reverse-transcribed from an mRNA population of interest. It is well within the skill of the person of skill in the art to design methodology directed to screening for either DNA or RNA. As detailed above, the method of the present invention also extends to screening for the protein product translated from the subject mRNA or the genomic DNA itself.

In one embodiment, the level of protein 14-3-3ζ expression is measured by reference to the mRNA or protein product.

In another embodiment, said gene expression is assessed by analysing genomic DNA methylation. In another embodiment, expression is assessed by the association of DNA with chromatin proteins carrying repressive modifications, for example, methylation of lysines 9 or 27 of histone H3.

The term "protein" should be understood to encompass peptides, polypeptides and proteins (including protein fragments). The protein may be glycosylated or unglycosylated and/or may contain a range of other molecules fused, linked, bound or otherwise associated to the protein such as amino acids, lipids, carbohydrates or other peptides, polypeptides or proteins. Reference herein to a "protein" includes a protein comprising a sequence of amino acids as well as a protein associated with other molecules such as amino acids, lipids, carbohydrates or other peptides, polypeptides or proteins.

Reference to a "fragment" should be understood as a reference to a portion of the subject nucleic acid molecule or protein. This is particularly relevant with respect to screening for modulated RNA levels since these are inherently unstable molecules and may be screened for in samples which express high levels of enzymes. In this case the subject RNA is likely to have been degraded or otherwise fragmented. One may therefore actually be detecting fragments of the subject RNA molecule, which fragments are identified by virtue of the use of a suitably specific probe.

Means of assessing protein 14-3-3ζ in a biological sample can be achieved by any suitable method, which would be well known to the person of skill in the art. To this end, it would be appreciated that to the extent that one is examining either a homogeneous cellular population or a tissue section, one may utilise a wide range of techniques such as in situ hybridisation, assessment of expression profiles by microassays, immunoassays and the like (hereinafter described in more detail) to detect the absence of or downregulation of the level of expression of one or more markers of interest. However, to the extent that one is screening a heterogenous cellular population or a bodily fluid in which heterogeneous populations of cells are found, such as a blood sample, the absence of or reduction in level of expression of protein 14-3-3ζ by a specific cellular subpopulation may be more difficult to detect due to inherent expression of protein 14-3-3ζ by other subpopulations of cells which are also present in the sample. That is, a decrease in the level of expression of a subgroup of cells may not be detectable. In this situation, a more appropriate mechanism, of detecting a reduction in the expression levels of protein 14-3-3ζ is via indirect means, such as the detection of epigenetic changes.

As detailed hereinbefore, during development gene expression is regulated by processes that alter the availability of genes for expression in different cell lineages without any alteration in gene sequence, and these states can be inherited through a cell division—a process called epigenetic inheritance. Epigenetic inheritance is determined by a combination of DNA methylation (modification of cytosine to give 5-methyl cytosine, 5 meC) and by modifications of the histone chromosomal proteins that package DNA. Thus methylation of DNA at CpG sites and modifications such as deacetylation of histone H3 on lysine 9, and methylation on lysine 9 or 27 are associated with inactive chromatin, while the converse state of a lack of DNA methylation, acetylation of lysine 9 of histone H3 is associated with open chromatin and active gene expression.

A variety of methods are available for detection of aberrantly methylated DNA of a specific gene, even in the presence of a large excess of normal DNA (Clark 2007). Thus, loss of expression of a gene which may be difficult to detect at the protein or RNA level except by immunohistochemistry can often be detected by the presence of hypermethylated DNA of the gene's promoter. Epigenetic alterations and chromatin changes are also evident in the altered association of modified histones with specific genes (Esteller, 2007); for example repressed genes are often found associated with histone H3 that is deacetylated and methylated on lysine 9. The use of antibodies targeted to altered histones allows for the isolation of DNA associated with particular chromatin states and its potential use in cancer diagnosis.

Other methods of detecting changes to gene expression levels include but are not limited to:
(i) In vivo detection.
Molecular Imaging may be used following administration of imaging probes or reagents capable of disclosing altered expression of protein 14-3-3ζ. Molecular imaging (Moore et al. *BBA*, 1402:239-249, 1988; Weissleder et al., *Nature Medicine* 6:351-355, 2000) is the in vivo imaging of molecular expression that correlates with the macro-features currently visualized using "classical" diagnostic imaging techniques such as X-Ray, computed tomography (CT), MRI, Positron Emission Tomography (PET) or endoscopy.
(ii) RNA screening
Detection of downregulation of RNA expression in cells by Fluorescent In Situ Hybridization (FISH), or in extracts from the cells by technologies such as Quantitative Reverse Transcriptase Polymerase Chain Reaction (QRTPCR) or Flow cytometric qualification of competitive RT-PCR products (Wedemeyer et al., *Clinical Chemistry* 48:9 1398-1405, 2002).
(iii) Assessment of expression profiles of RNA, for example by array technologies (Alon et al., *Proc. Natl. Acad. Sci. USA:* 96, 6745-6750, June 1999).

A "microarray" is a linear or multi-dimensional array of preferably discrete regions, each having a defined area, formed on the surface of a solid support. The density of the discrete regions on a microarray is determined by the total numbers of target polynucleotides to be detected on the surface of a single solid phase support. As used herein, a DNA microarray is an array of oligonucleotide probes placed onto a chip or other surfaces used to, amplify or clone target polynucleotides. Since the position of each particular group of probes in the array is known, the identities of the target polynucleotides can be determined based on their binding to a particular position in the microarray.

Recent developments in DNA microarray technology make it possible to conduct a large scale assay of a plurality of target nucleic acid molecules on a single solid phase support. U.S. Pat. No. 5,837,832 (Chee et al.) and related patent applications describe immobilizing an array of oligonucleotide probes for hybridization and detection of specific nucleic acid sequences in a sample. Target polynucleotides of interest isolated from a tissue of interest are hybridized to the DNA chip and the specific sequences detected based on the target polynucleotides' preference and degree of hybridization at discrete probe locations. One important use of arrays is in the analysis of differential gene expression, where the profile of expression of genes in different cells or tissues, often a tissue of interest and a control tissue, is compared and any differences in gene expression among the respective tissues are identified. Such information is useful for the identification of the types of genes expressed in a particular tissue type and diagnosis of conditions based on the expression profile.

The arrays may be produced according to any convenient methodology, such as preforming the polynucleotide microarray elements and then stably associating them with the surface. Alternatively, the oligonucleotides may be synthesized on the surface, as is known in the art. A number of different array configurations and methods for their production are known to those of skill in the art and disclosed in WO 95/25116 and WO 95/35505 (photolithographic techniques), U.S. Pat. No. 5,445,934 (in situ synthesis by photolithography), U.S. Pat. No. 5,384,261 (in situ synthesis by mechanically directed flow paths); and U.S. Pat. No. 5,700,637 (synthesis by spotting, printing or coupling); the disclosure of which are herein incorporated in their entirety by reference. Another method for coupling DNA to beads uses specific ligands attached to the end of the DNA to link to ligand-binding molecules attached to a bead. Possible ligand-binding partner pairs include biotin-avidin/streptavidin, or various antibody/antigen pairs such as digoxygenin-antidigoxygenin antibody (Smith et al., Science 258:1122-1126 (1992)). Covalent chemical attachment of DNA to the support can be accomplished by using standard coupling agents to link the 5'-phosphate on the DNA to coated microspheres through a phosphoamidate bond. Methods for immobilization of oligonucleotides to solid-state substrates are well established. See Pease et al., Proc. Natl. Acad. Sci. USA 91(11):5022-5026 (1994). A preferred method of attaching oligonucleotides to solid-state substrates is described by Guo et al., Nucleic Acids Res. 22:5456-5465 (1994). Immobilization can be accomplished either by in situ DNA synthesis (Maskos and Southern, Nuc. Acids Res. 20:1679-84, 1992) or by covalent attachment of chemically synthesized oligonucleotides (Guo et al., supra) in combination with robotic arraying technologies.

In addition to the solid-phase technology represented by biochip arrays, gene expression can also be quantified using liquid-phase arrays. One such system is kinetic polymerase chain reaction (PCR). Kinetic PCR allows for the simultaneous amplification and quantification of specific nucleic acid sequences. The specificity is derived from synthetic oligonucleotide primers designed to preferentially adhere to single-stranded nucleic acid sequences bracketing the target site. This pair of oligonucleotide primers form specific, non-covalently bound complexes on each strand of the target sequence. These complexes facilitate in vitro transcription of double-stranded DNA in opposite orientations. Temperature cycling of the reaction mixture creates a continuous cycle of primer binding, transcription, and re-melting of the nucleic acid to individual strands. The result is an exponential increase of the target dsDNA product. This product can be quantified in real time either through the use of an intercalating dye or a sequence specific probe. SYBR(r) Green 1, is an example of an intercalating dye, that preferentially binds to dsDNA resulting in a concomitant increase in the fluorescent signal. Sequence specific probes, such as used with TaqMan technology, consist of a fluorochrome and a quenching molecule covalently bound to opposite ends of an oligonucleotide. The probe is designed to selectively bind the target DNA sequence between the two primers. When the DNA strands are synthesized during the PCR reaction, the fluorochrome is cleaved from the probe by the exonuclease activity of the polymerase resulting in signal dequenching. The probe signalling method can be more specific than the intercalating dye method, but in each case, signal strength is proportional to the dsDNA product produced. Each type of quantification method can be used in multi-well liquid phase arrays with each well representing primers and/or probes specific to nucleic acid sequences of interest. When used with messenger RNA preparations of tissues or cell lines, an array of probe/primer reactions can simultaneously quantify the expression of multiple gene products of interest. See Germer et al., Genome Res. 10:258-266 (2000); Heid et al., Genome Res. 6:986-994 (1996).

(iv) Measurement of altered protein 14-3-3ζ levels in cell extracts, for example by immunoassay.

Testing for proteinaceous neoplastic marker expression product in a biological sample can be performed by any one of a number of suitable methods which are well known to those skilled in the art. Examples of suitable methods include, but are not limited to, antibody screening of tissue sections, biopsy specimens or bodily fluid samples. To the extent that antibody based methods of diagnosis are used, the presence of the protein may be determined in a number of ways such as by Western blotting, ELISA or flow cytometry procedures. These, of course, include both single-site and two-site or "sandwich" assays of the non-competitive types, as well as in the traditional competitive binding assays. These assays also include direct binding of a labelled antibody to a target.

Sandwich assays are a useful and commonly used assay. A number of variations of the sandwich assay technique exist, and all are intended to be encompassed by the present invention. Briefly, in a typical forward assay, an unlabelled antibody is immobilized on a solid substrate and the sample to be tested brought into contact with the bound molecule. After a suitable period of incubation, for a period of time sufficient to allow formation of an antibody-antigen complex, a second antibody specific to the antigen, labelled with a reporter molecule capable of producing a detectable signal is then added and incubated, allowing time sufficient for the formation of another complex of antibody-antigen-labelled antibody. Any unreacted material is washed away, and the presence of the antigen is determined by observation of a signal produced by the reporter molecule. The results may either be qualitative, by simple observation of the visible signal, or may be quantitated by comparing with a control sample. Variations on the forward assay include a simultaneous assay, in which both sample and labelled antibody are added simultaneously to the bound antibody. These techniques are well known to those skilled in the art, including any minor variations as will be readily apparent.

In the typical forward sandwich assay, a first antibody having specificity for the marker or antigenic parts thereof, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking, covalently binding or physically adsorbing, the polymer-antibody complex is washed in preparation for the test sample. An aliquot of the sample to be tested is then added to the solid phase complex and incubated for a period of time sufficient (e.g. 2-40 minutes) and under suitable conditions (e.g. 25° C.) to allow binding of any subunit present in the antibody. Following the incubation period, the antibody subunit solid phase is washed and dried and incubated with a second antibody specific for a portion of the antigen. The second antibody is linked to a reporter molecule which is used to indicate the binding of the second antibody to the antigen.

An alternative method involves immobilizing the target molecules in the biological sample and then exposing the immobilized target to specific antibody which may or may not be labelled with a reporter molecule. Depending on the amount of target and the strength of the reporter molecule signal, a bound target may be detectable by direct labelling with the antibody. Alternatively, a second labelled antibody, specific to the first antibody is exposed to the target-first antibody complex to form a target-first antibody-second antibody tertiary complex. The complex is detected by the signal emitted by the reporter molecule.

By "reporter molecule" as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e. radioisotopes) and chemiluminescent molecules.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chosen for the production, upon hydrolysis by the corresponding enzyme, of a detectable color change. Examples of suitable enzymes include alkaline phosphatase and peroxidase. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the complex of antibody-antigen-antibody. The substrate will react with the enzyme linked to the second antibody, giving a qualitative visual signal, which may be further: quantitated, usually spectrophotometrically, to give an indication of the amount of antigen which was present in the sample. "Reporter molecule" also extends to use of cell agglutination or, inhibition of agglutination such as red blood cells on latex beads, and the like.

Alternately, fluorescent compounds, such as fluorecein and rhodamine, may be chemically coupled to antibodies without altering their binding capacity. When activated by illumination with light of a particular wavelength, the fluorochrome-labelled antibody adsorbs the light energy, inducing a state to excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength the fluorescence observed indicates the presence of the hapten of interest. Immunofluorescence and EIA techniques are both very well established in the art and are particularly preferred for the present method. However, other reporter molecules, such as radioisotope, chemiluminescent or bioluminescent molecules, may also be employed.

(v) Determining altered protein expression based on any suitable functional test, enzymatic test or immunological test in addition to those detailed in points (iv) above.

(vi) To the extent that one is screening for protein 14-3-3ζ/DISC1 complex formation, a variety of methods could be used including immobilising one or other molecule on a solid support and then exposing the immobilised target to the biological sample and screening for complex formation. Such screening techniques are generally described hereinbefore. Co-immunoprecipitation techniques may also conveniently be utilised. Alternatively, a biocore protein interaction system could be used.

As detailed hereinbefore, it would be appreciated by the skilled person that designing the assays for detecting complex formation may require the inclusion of molecules other than just DISC1 and protein 14-3-3ζ since Nedl1 and LIS1 are also involved in the formation of the functional complex. The design of such an assay would be well within the skill of the person in the art.

In the context of these types of screening methods, it would be appreciated that their advantage is that one need not necessarily know the nature of the defect which may exist in either or both of the protein 14-3-3ζ molecule or the DISC1 molecule. Rather, since one is merely screening for the occurrence of complex formation or co-immunoprecipitation, or not, the identity of the defect becomes irrelevant.

A related aspect of the present invention provides non-human mammals in which protein 14-3-3ζ gene expression has been knocked out. The development of such animals facilitates the screening for and analysis of therapeutically and/or prophylactically effective proteinaceous or non-proteinaceous molecules which may modulate the onset and progression of a neuropsychiatric disorder, such as the schizophrenic phenotype. This development now provides an extremely valuable means for, inter alia, studying the functional role of protein 14-3-3ζ in relation to the onset of schizophrenia and rationally designing prophylactic and/or therapeutic treatment regimes.

Accordingly, another aspect of the present invention is directed to a non-human mammal deficient in functional protein 14-3-3ζ in which a gene encoding protein 14-3-3ζ has been deleted.

The term "phenotype" should be understood as a reference to the totality of the functional and structural characteristics, or any particular characteristic or set of characteristics, of an animal as determined by interaction of the genotype of the organism with the environment in which it exists. In the context of the present invention, the subject phenotype is the onset of schizophrenia, a predisposition to the onset of schizophrenia or the onset/predisposition to the onset of one or more symptoms associated with schizophrenia. This phenotype is herein referred to as a "schizophrenia phenotype".

Preferably, said non-human mammal is a mouse.

It should be understood that the present invention also provides cells and cell lines comprising the 14-3-3ζ knockout described above. These cells/cell lines may be derived from any suitable source, or may be generated by any suitable means.

The development of the mammals (herein referred to as a "14-3-3ζ knockout") of the present invention now facilitates a wide variety of highly useful applications including, but not limited, to screening methods to identify agents which mimic protein 14-3-3ζ functionality or 14-3-3ζ/DISC1 complex formation or otherwise improve the symptoms of schizophrenic phenotype of these mammals.

Accordingly, yet another aspect of the present invention is directed to a method of screening for an agent which mimics protein 14-3-3ζ functionality or 14-3-3ζ/DISC1 complex formation or otherwise improves the symptoms of a schizophrenic phenotype, said method comprising administering to a 14-3-3ζ knockout non-human animal a putative modulation agent and screening for altered phenotype.

Reference to an "agent" should be understood as a reference to any proteinaceous or non-proteinaceous molecule derived from natural, recombinant or synthetic sources including fusion proteins or following, for example, natural product screening and which achieves the object of the present invention. Synthetic sources of said agent include for example chemically synthesised molecules. In other examples, phage display libraries can be screened for peptides while chemical libraries can be screened for existing small molecules.

By way of example, diversity libraries, such as random combinatorial peptide or nonpeptide libraries can be screened. Many publicly or commercially available libraries can be used such as chemically synthesized libraries, recombinant (e.g., phage display libraries) and in vitro translation-based libraries.

Examples of chemically synthesized libraries are described in Fodor et al. *PNAS USA* 91:11422-26 (1991); Houghten et al. *Nature* 354:84-88 (1991); Lam et al. *Nature* 354:82-84 (1991); Medynski, *Bio/Technology* 12:709-710 (1994); Gallop et al. *J. Medicinal Chemistry* 37(9):1233-1251 (1994); Ohlmeyer et al. *PNAS USA* 91:9022-9026 (1993); Erb et al. *PNAS USA* 91:11422-26 (1994); Houghten et al. *Biotechniques* 13(3):412-421 (1992); Jayawickreme et al. *PNAS USA* 91:1614-1618 (1994); Salmon et al. *PNAS USA* 90:11708-11712 (1993): International Patent Publication No. WO 93/20242; and Brenner and Lerner, *PNAS USA* 89:5381-3 (1992).

Examples of phage display libraries are described by Scott and Smith, *Science* 249:386-390 (1990); Devlin et al. *Science* 249:404-406 (1990); Christian et al. *J. Mol. Biol.* 227:711-718 (1992); Lenstra, *J. Immun. Methods* 152:149-157 (1992); Kay et al. *Gene* 128:59-65 (1993) and International Patent Publication No. WO 94/18318.

In vitro translation-based libraries include but are not limited to those described in Mattheakis et al. *PNAS USA* 91:9022-9026 (1994).

Without limiting the present invention in any way a test compound can be a macromolecule, such as biological polymer, including polypeptides, polysaccharides and nucleic acids. Compounds useful as potential therapeutic agents can be generated by methods well known those skilled in the art, for example, well known methods for producing pluralities of compounds, including chemical or biological molecules such as simple or complex organic molecules, metal-containing compounds, carbohydrates, peptides, proteins, peptidomimetics, glycoproteins, lipoproteins, nucleic acids, antibodies, and the like, are well known in the art and are described, for example, in Huse, U.S. Pat. No. 5,264,563; Francis et al., *Curr. Opin. Chem. Biol.*, 2:422-428 (1998); Tietze et al., *Curr. Biol.* 2:363-381 (1998); Sofia, *Molecule. Divers.*, 3:75-94 (1998); Eichler et al., *Med. Res. Rev.* 15:481-496 (1995); and the like. Libraries containing large numbers of natural and synthetic compounds also can be obtained from commercial sources. Combinatorial libraries of molecules can be prepared using well known combinatorial chemistry methods (Gordon et al., *J. Med. Chem.* 37: 1233-1251 (1994); Gordon et al., *J. Med. Chem.* 37:1385-1401 (1994); Gordon et al., *Acc. Chem. Res.* 29:144-154 (1996); Wilson and Czarnik, eds., *Combinatorial Chemistry: Synthesis and Application*, John Wiley & Sons, New York (1997).

Reference to detecting an "altered expression phenotype" should be understood as the detection of any form of change associated with modulation of 14-3-3ζ functioning. These may be detectable, for example, as intracellular changes, changes observed extracellularly (for example, detecting changes in downstream product levels or activities) or changes in the phenotype/condition of the non-human mammalian subject. For example, subsequently to administering the agent to the 14-3-3ζ knockout mouse of the present invention, one may perform one or more of the behavioural assays described in Example 1, such as:
  (i) locomotor function test;
  (ii) object recognition test
  (iii) elevated cross bar test
  (iv) escape water maze test; or
  (v) PPI test.

If more detailed molecular tests are required to be performed to validate or otherwise further investigate phenotypic changes observed at the behavioural level, then cells or tissues can be harvested from the subject knockout animals in order to enable more detailed analyses which are performed at the cellular or molecular level. Alternatively, one may test cell lines generated from these animals.

It should be understood that these aspects of the present invention provide not only a means of screening for novel agents which modulate the schizophrenia phenotype of individuals exhibiting impaired 14-3-3ζ functioning, but also provide a means of assessing the benefit/side effects of existing treatment regimes in the context of this group of patients.

The present invention is further described by reference to the following non-limiting examples.

Example 1

Materials and Methods
Mice.

14-3-3ζ$^{Gt(OST062)Lex}$ and 14-3-3ζ$^{Gt(OST390)Lex}$ mutant mice carrying gene trap constructs that contain the Geo reporter gene were derived from LexiCon Genetics ES cell lines OST062 and OST390, respectively. The gene trap vector in 14-3-3ζ$^{Gt(OST062)Lex}$ mice inserted into the first intron of 14-3-3ζ, whereas the gene trap vector in 14-3-3ζ$^{Gt(OST390)Lex}$ mice inserted into the second intron of 14-3-3ζ. ES cell lines were amplified and injected into SV129 blastocysts. Resulting germ line transmitting males were either maintained in the SV129 background or back-crossed in to the C57/B16 and BALBC backgrounds over 6 generations, qRT-PCR and western blot from whole tissue samples was used to confirm complete KO of the gene in these mouse strains. 14-3-3ζ genotype was determined by PCR amplification of genomic tail DNA using the primers detailed in supplementary table 1. The WT allele amplified a band of 288 bp (14-3-3ζ$^{Gt(OST062)Lex}$) or 445 bp (14-3-3ζ$^{Gt(OST390)Lex}$) and the mutant gene trapped allele amplified a band of 165 bp (14-3-3ζ$^{Gt(OST062)Lex}$) or 203 bp (14-3-3ζ$^{Gt(OST390)Lex}$). Mice were maintained as heterozygous breeding pairs that were phenotypically indistinguishable to WT littermates. Animal experiments were conducted in accordance with the guidelines of the Animal Ethics Committee of the Institute of Medical and Veterinary Sciences and the University of Adelaide.

Behavioural Assays.

All procedures were carried out under normal light conditions between 8.00 am and 12.00 pm. Behavioural phenotyping was performed as previously described (Coyle et al. *Behav Brain Res* 2009, 197(1): 210-218; Summers et al. *Pediatr Res* 2006; 59(1): 66-71; van den Buuse et al. *Int J Neuropsychopharmacol* 2009; 12(10):1383-1393). One cohort of mice was used for the open field test at ages of 5-, 10-, 20- and 40-week time points. One cohort of mice was used at the age of 12 weeks for spatial working memory, then elevated plus maze and object recognition tasks. A separate cohort of mice was used at the age of 12 weeks for PPI.

Locomotor Function Test.

Exploratory activity and anxiety level of mice were measured in an open field made from a box (50 cm×27 cm) with the floor divided into 15 squares (9 cm×10 cm). Each mouse was introduced in to the same position of the box facing the right top corner. The behaviour of the mouse was observed for 3 min and locomotor activity was scored as a measure of line crossings (i.e. when a mouse removed all four paws from one square into another). Number of rears up was scored when a mouse had both front paws off the floor.

Urine and faecal material were removed between session and the box was cleaned thoroughly with 80% ethanol to remove any lingering scents.

Object Recognition Test.

The object recognition task takes advantage of the natural affinity of mice for novelty; mice that recognise a previously seen (familiar) object will spend more time exploring novel objects (Dere et al. *Neurosci Biobehav Rev* 2006; 30(8): 1206-1224; Sik et al. *Behav Brain Res* 2003; 147(1-2):49-54). Briefly, the apparatus consisted of a plastic arena (length; 50 cm, width; 35 cm, depth; 20 cm) filled with bedding. Two different sets of objects were used; a yellow-capped plastic jar (height, 6 cm; base diameter, 4.3 cm) and a red plastic bulb (length: 8 cm, width: 4 cm). Mice spent equal amounts of time when presented with both of these objects, regardless of the position they were placed in the arena (data not shown). At 12 weeks of age the same cohort of mice tested for spatial learning and memory were assessed for object recognition memory. Each mouse was given 5-min to explore the test box without any objects present to habituate them to the test arena. Mice underwent the testing session comprised of two trials. The duration of each trial was 3 min. During the first trial (the sample phase), the box contained two identical objects (a, samples) which were placed in the north-west (left) and northeast (right) corners of the box (5 cm away from the walls). A mouse was always placed in the apparatus facing the south wall. After the first exploration period, mice were placed back in their homecage. After a 15-min retention interval, the mouse was placed in the apparatus for the second trial (choice phase), but now with a familiar one (a. sample) and a novel object (b). The objects were cleaned thoroughly with alcohol between sessions to remove any lingering scents. The time spent exploring each object during trial 1 and trial2 was recorded. Exploration was defined as either touching the object with the nose or being within 2 cm of it. The basic measures in the object recognition task were the times spent exploring an object during trial 1 and trial 2. Several variables were measured during the tests: e1 (a+a) and e2 (a+b) are measures of the total exploration time of both objects during trial 1 and trial 2, respectively. h1 is an index of habituation measured by the difference in total exploration time from trial 1 to trial 2(e1−e2). d1 (b−a) and d2 (d1/e2) were considered as index measures of discrimination between the novel and the familiar objects. Thus, d2 is a relative measure of discrimination that corrects d1 for exploratory activity (e2). A discrimination index above zero describes animals exploring the novel object more than the familiar object. An animal with no preference for either object will have an index near zero. Mice with a total exploration time of less than 7 s during trials in the sample or choice phase were excluded from the analyses as the measurement of exploration time has been found to be non-reliable below this threshold (van den Buuse et al. supra; de Bruin et al. *Pharmacol Biochem Behav* 2006; 85(1):253-260).

Elevated Cross Bar Test.

The anxiety behaviour of mice based on their natural aversion of open and elevated areas was assessed using an elevated plus-maze as previously described (Komada et al. *J Vis Exp* 2008; (22); Walf et al. *Nat Protoc* 2007; 2(2):322-328). Briefly, the apparatus was made in the shape of a cross from black plexiglass and consisted of two open arms (25 cm×5 cm) and two closed arms (25 cm×5 cm×16 cm) that crossed in the middle perpendicular to each other. In the middle of the to arms there was a central platform (5 cm×5 cm). The cross maze was raised 1 m from the ground. Individual mice were introduced to the center of the apparatus facing the open arm opposite to the experimenter were and observed by video recording for 5 minutes. The number of entries into the open and closed arms and the time in exploring both types of arm were scored. Naturalistic behaviour of the mouse such as the number of head dipping, number of rearing and number of stretch attended postures were measured. After each trial all arms and the central area thoroughly cleaned with alcohol to remove any lingering scents.

Escape Water Maze Test.

Spatial learning and memory was assessed using a cross-maze escape task as previously described (Coyle et al. 2009, supra). The cross maze was made of a clear plastic (length, 72 cm; arm dimensions, length 26 cm×width 20 cm) and placed in a circular pool of water (1 m diameter) maintained at 23 C. Milk powder was mixed into the water to conceal a submerged (0.5 cm below the water surface) escape platform placed in the distal north arm of the maze. The pool was enclosed by a black plastic wall (height, 90 cm). Constant spatial cues were arranged at each arm of the maze and by the experimenter who always stood at the southern end during the training and testing procedures. 12 week old mice were individually habituated to the maze environment by being placed into the pool without the escape platform and allowed to swim for 60 s. Learning trials were conducted over a 6-day training period in which mice were required to learn the position of the submerged escape platform from the other three (East, South, West) arms that did not contain an escape platform. Each mouse was given six daily trials (two blocks of three trials separated by a 30 min rest interval), in which each of the three arms were chosen as a starting point in a randomized pattern (twice daily). For each trial, the mouse was placed in the distal end of an arm facing the wall and allowed 60 s to reach the escape platform where it remained for 10 s. Mice that did not climb onto the escape platform in the given time were placed on the platform for 10 s. The mouse was then placed in a cage for 10 s and subsequent trials were continued. Mice were assessed on their long-term retention of the escape platform location which was placed in the same position as during the learning phase. Memory was tested 14 (M1) and 28 (M2) days after the final day of learning and consisted of a single day of 6 trials as described for the learning period. Data were recorded for each mouse for each trial on their escape latency (i.e. time (s) taken to swim to the platform), number of correct trials (i.e. if a mouse found the platform on the first arm entry) and number of incorrect entries/reentries (i.e. the number of times that a mouse went into an arm that did not contain the escape platform).

PPI Test.

Startle, startle habituation and PPI of startle were assessed using an eight-unit automated system (SR-LAB, San Diego Instruments, USA) as previously described (van den Buuse et al. 2009 supra). Briefly, mice were placed in clear Plexiglas cylinders which were closed on either side and acoustic stimuli were delivered over 70-dB background noise through a speaker in the ceiling of the box. Eacl: testing session consisted of 104 trials with an average inter-trial interval between 25 s. The first and last eight trials consisted of single 40-ms 115-dB pulse alone startle stimuli. The middle 88 trials consisted of pseudo-randomised delivery of 16 115-dB pulse-alone stimuli, eight trials during which no stimulus was delivered, and 64 prepulse trials. The total of 32 115-dB pulse alone trials was expressed as four blocks of eight and used to determine startle habituation. Prepulse trials consisted of a single 115-dB pulse preceded by a 30-ms or 100-ms inter-stimulus interval (ISI) with a 20-ms non-startling stimulus of 2, 4, 8 or 16 dB over the 70-dB baseline. Whole-body startle responses were converted into quantitative values by a piezo-electric accelerometer unit attached beneath the platform. Percentage prepulse inhibition (% PPI) was calculated as pulse-alone startle response−prepulse+pulse startle response/pulse-alone startle response×100.

Statistical Analysis.

All statistical calculations are presented as mean±SEM and were performed using SAS Version 9.2 (SAS Institute Inc., Cary, N.C., USA). For open field data the number of line crossings were compared across the WT and mutant groups and over time using a linear mixed effects model. A random mouse effect was included in the model to account for the dependence in repeated observations from the same mouse. Data from the elevated cross bar was compared between WT and mutants using an independent samples t-test. For the water cross-maze test escape latency was compared between the two treatment groups and over time using a Cox proportional hazards model. Robust variance estimation was used in the model to adjust for the dependence in results due to repeated measurements on the same mouse. In the model group (WT or KO), time (days 1 to 6) and the interaction between group and time were entered as predictor variables. Escape latency was considered right censored at 30 seconds when a mouse had yet to find the exit. In our study there were too many animals with an escape latency censored at 30 seconds to be able to treat the outcome as being normally distributed. Thus it was not feasible to use a linear mixed effects model. Incorrect entries were compared between WT and mutant groups and over time using a negative binomial regression model. In the model group (WT or KO), time (days 1 to 6) and the interaction between group and time were entered as predictor variables. A generalised estimating equation was used to account for the dependence in results cue to repeated measurements on the same mouse. Data from the PPI tests were compared using two-way analysis of variance (ANOVA) with repeated measures (Systat, version 9.0, SPSS software; SPSS Inc., USA). For this analysis the between-group factor was genotype and the within group, repeated-measures factors were prepulse intensity and startle block. In all studies ap value of <0.05 was considered to be statistically significant.

Immunohistochemistry.

Sections were blocked in 10% non-immune horse serum in PBST (0.1M PBS, 0.3% Triton X-100, 1% BSA) for 1 h at room temperature (RT) and subsequently incubated with primary antibodies overnight at RT. Primary antibodies and dilutions: rabbit polyclonal to 14-3-3ζ (1:200) (Guthridge et al. *Blood* 2004; 103(3):820-827), rabbit polyclonal to 0-tubulin (1:250, Sigma), rabbit polyclonal to calbindin-D28K (1:1000, Chemicon), mouse monoclonal to NeuN (1:500, Chemicon), rabbit polyclonal to synaptophysin (1:100, Cell Signaling). On the following day, sections were incubated with secondary antibodies for 1 h at RT. After 3 times 0.1M PBS wash, the sections were mounted in Prolong® Gold antifade reagent with DAPI (Molecular Probes).

BrdU-Pulse-Chase Analysis and TUNEL Labelling.

BrdU was injected at 100 μg/g of body weight of the pregnant mice at 14.5 dpc or 16.5 dpc and the pups were euthanized at postnatal-day-7. Final destination, of the proliferating hippocampal neurons that were born at these time points were revealed by BrdU immunohistochemistry on frozen brain sections. Tissue were denatured with 2M HCl for 20 min at 37° C., neutralised in 0.1 M borate buffer (pH 8.5) for 10 min, blocked with 10% horse serum in PBST and probed with rat monoclonal anti-Brd1.1 (1:250; Abcam) and mouse monoclonal anti-NeuN (1:500; Chemicon) antibodies overnight at 4° C.: Cell apoptosis was determined by the TUNEL assay using the In Situ Cell Death Detection Kit (TMR Red; Roche Applied Science) according to the manufacturer's instructions followed by counterstained with DAPI (Molecular Probes).

Immunoprecipitation.

All protein extracts were prepared by lysis in NP40 lysis buffer composed of 150 mM NaCl, 10 mM Tris-HCl (pH 7.4), 10% glycerol, 1% Nonidet P-40, and protease and phosphatase inhibitors (10 mg of aprotinin per ml, 10 mg of leupeptin per ml, 2 mM phenylmethylsulfonyl fluoride, and 2 mM sodium vanadate). Samples were lysed for 60 min at 4 C, then centrifuged at 10,000 g for 15 min. The supernatants were prepared with mouse Ig-coupled Sepharose beads for 30 min at 4 C. The precleared lysates were incubated for 2 h at 4 C with 2 ug/ml of either anti-DISC1 antibody (C-term) (Invitrogen) or anti-14-3-3 antibody (3F7 Abeam) absorbed to protein A-Sepharose (Amersham Biosciences). The sepharose beads were washed 3 times with lysis buffer before being boiled for 5 min in SDS-PAGE sample buffer. The immunoprecipitated proteins and lysates were separated by SDS-PAGE, and electrophoretically transferred to a nitrocellulose membrane and analysed by immunoblotting.

Immunoblotting.

The membranes were probed with either anti-14-3-3ζ EB1 pAb at 1:1000 (Guthridge et al. 2004 supra) or anti DISC1 (C-term) (Invitrogen) at 1 ug/ml.). For analysis of 14-3-3ζ from brain tissue rabbit polyclonal against the (3-actin (1:5000, Millipore) was used as a loading control. Bound antibodies were detected with HRP-conjugated secondary antibody (1:20,000, Pierce-Thermo Scientific). Immunoreactive proteins were visualized by ECL (Luminescent Image Analyzer LAS-4000, Fujifilm, Japan). The images were analysed with Multi Gauge Ver3.0 (Fujifilm, Japan).

Neuronal Cell Cultures.

P7 hippocampi neuron-glial cocultures were prepared as described (Kaech et al. *Nat Protoc* 2006, 1(5):2406–2415). Nitric acid-treated coverslips (diameter 13 mm) were coated with 100 μg/ml poly-L-lysin/PLL (Sigma) in borate buffer for overnight at 37° C., and were then washed with sterile water for 3×1 h. Dentate gyri and CA samples were dissected and dissociated in Hank's balanced salt solution (HBSS) and neurons were plated at a density of $1 \times 10^5$ cells per culture dish (with 4 PLL-coated coverslips). Cultures were incubated for 7 and 14 days in vitro for neurite outgrowth assay. Cells were fixed in 4% PFA for 1 h, preincubated in 10% non-immune horse serum in PBST (0.1M PBS, 0.1% Triton X-100, 1% BSA) for 1 h at room temperature (RT) and incubated overnight at 4° C. with primary antibodies against mouse monoclonal MAP2 (1:200, Millipore) and 14-3-3ζ (1:1000). The coverslips were then incubated with the corresponding secondary antibodies for 1 h at RT. Coverslips were mounted with anti-fade DAPI (Molecular Probes).

Figure 8:
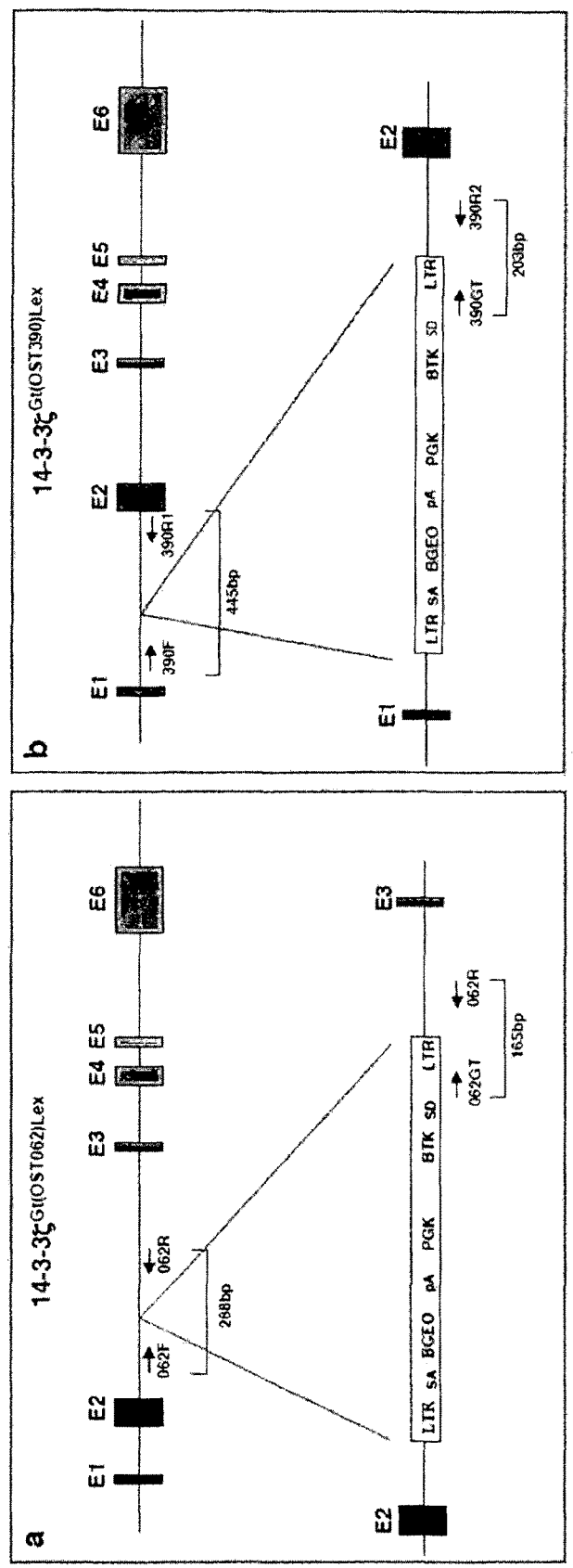
FIG. 8: Gene trap mutation of the 14-3-3$\zeta$ gene. (a) Schematic showing the insertion point for mouse line 14-3-3$\zeta^{Gt(OST062)Lex}$ and (b) for mouse line 14-3-3$\zeta^{Gt(OST390)Lex}$. The gene trap vector contains a splice acceptor sequence (SA) fused to a selectable marker gene (BGEO for 0 galactosidase/neomycinphosphotransferase fusion gene) that is thereby expressed under the endogenous 14-3-3$\zeta$ promoter. When integrated into the upstream exons of 14-3-3$\zeta$ BGEO produces a fusion transcript that interrupts mRNA transcription. The vectors also contain a PGK promoter followed by the first exon of Bruton's Tyrosine Kinase gene (BTK) upstream of a splice donor (SD) signal. BTK contains termination codons in all reading frames to prevent translation of downstream fusion transcripts. The gene trap vector is depicted in retrovirus form between two long terminal repeats (LTR). On both figures, arrows denote primers used for genotyping. Red boxes indicate non-coding untranslated sequence and green boxes denote coding sequence.
Figure 9:
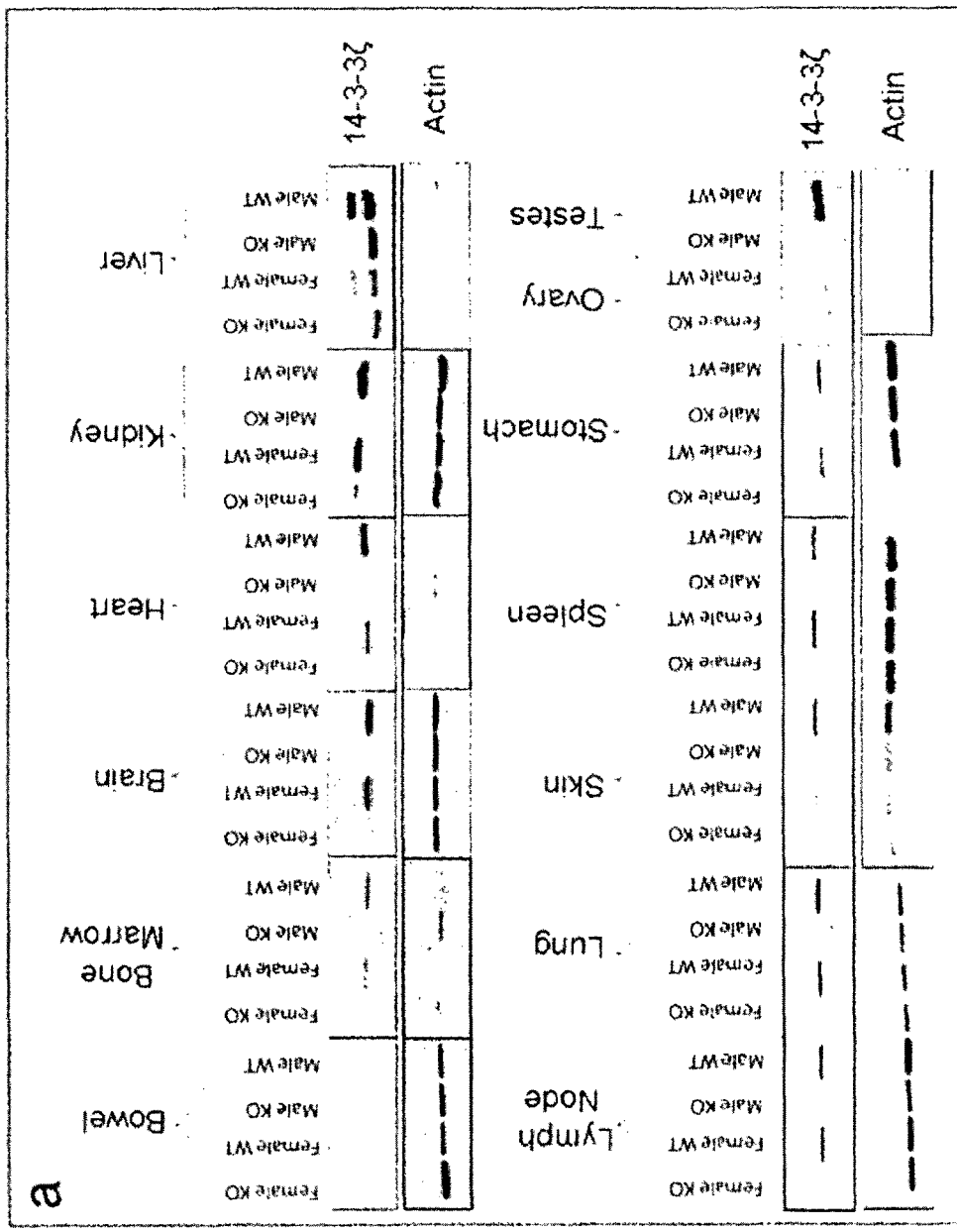
FIG. 9: Western Blot analysis demonstrates that 14-3-3$\zeta$ expression is reduced in all tissues of mutant mice: Tissues were harvested from (a) both male and female 14-3-3$\zeta^{062-/-}$ and age-matched 14-3-3$\zeta^{062+/+}$ mice and from (b) both male and female 14-3-3$\zeta^{390-/-}$ and age-matched 14-3-3$\zeta^{390+/+}$ mice. All samples were homogenised in NP40 lysis buffer containing protease inhibitors as described in the Materials and Methods. Protein concentrations were determined using Pierce BCA Protein Assay kit and 10 μg protein was loaded per lane. Blots were probed with EB-1 antibody to detect 14-3-3$\zeta$ and anti-β-actin (1:5000) was used as a loading control. Bound antibodies were detected with HRP-conjugated secondary antibody (1:20,000, Pierce-Thermo Scientific). Immunoreactive proteins were visualized by ECL. Note that EB1 antibody may also detect 14-3-3 isoforms other than 14-3-3$\zeta$.
Figure 9:
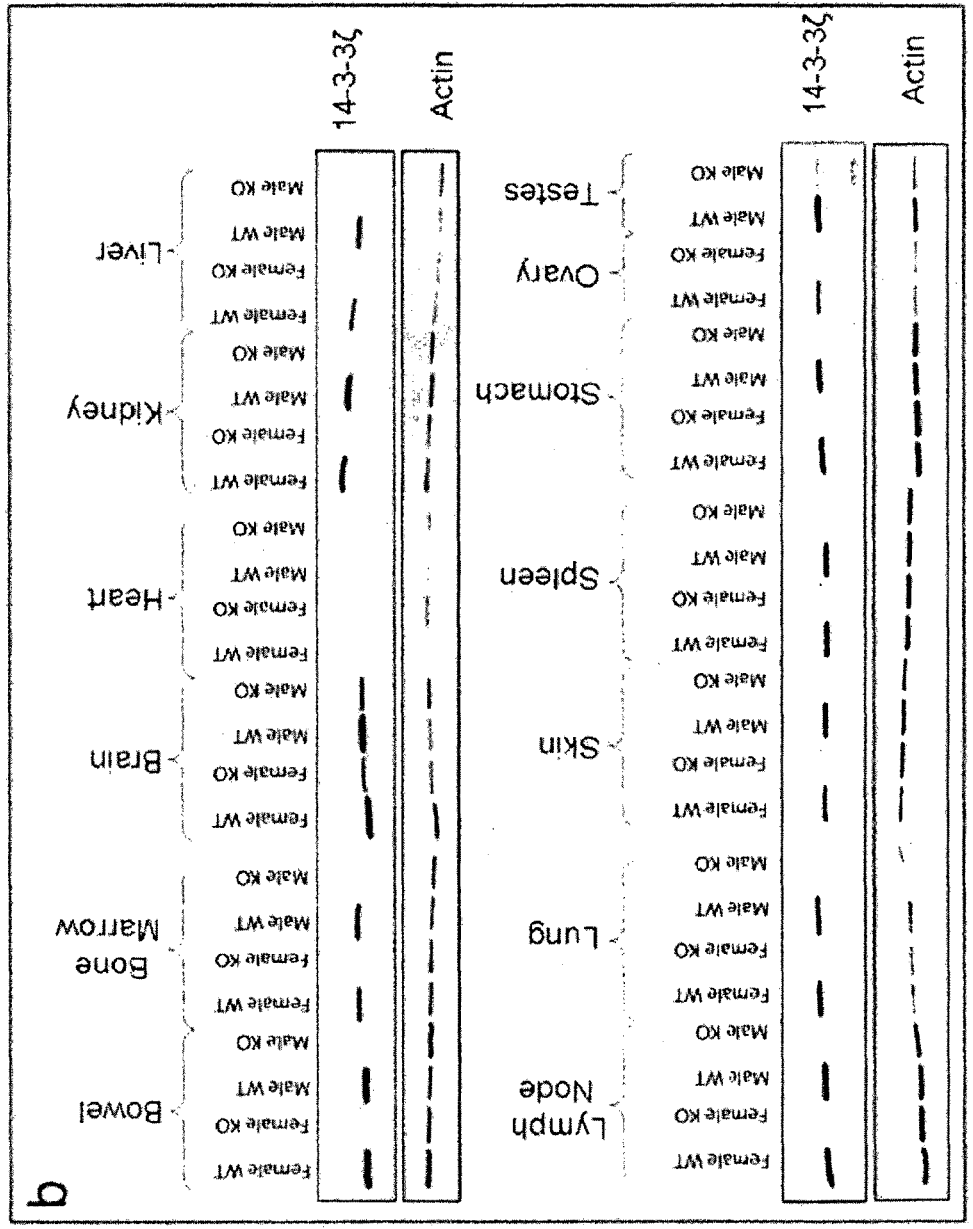
Figure 10:
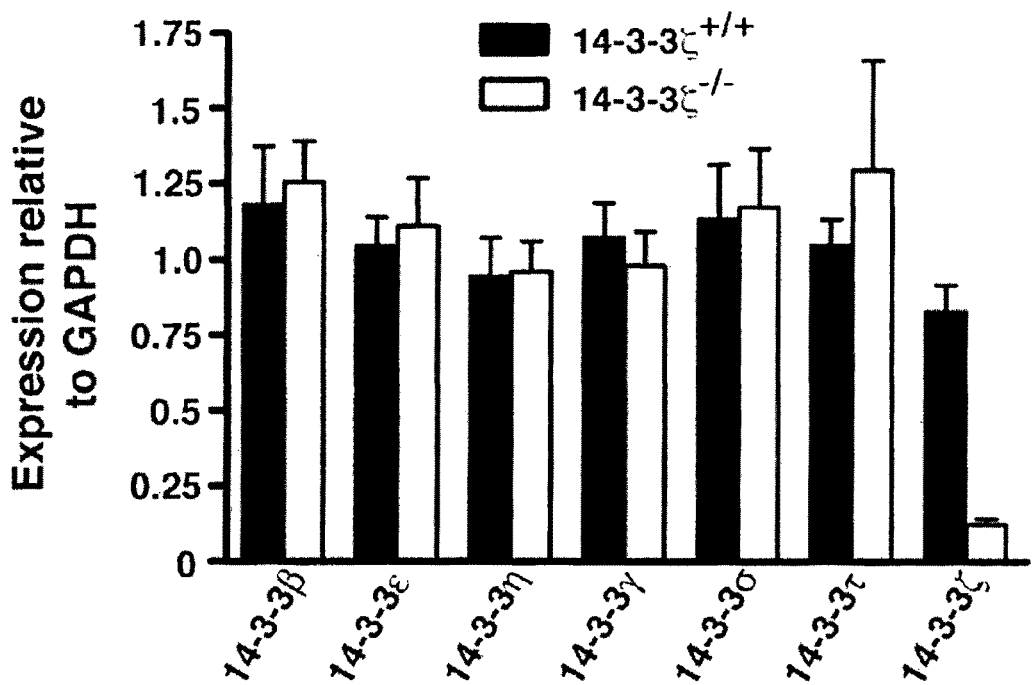
FIG. 10: mRNA levels of 14-3-3 isoforms remain constant in 14-3-3$\zeta$-deficient mouse brain: Transcript levels of all 14-3-3 isoforms are unchanged in response to the deletion of the 14-3-3$\zeta$ isoform in brain tissue from 14-3-3$\zeta^{062-/-}$ mice. RNA was isolated from whole brain of three 14-3-3-$\zeta^{062-/-}$ mice and three age-matched 14-3-3$\zeta^{062+/+}$ controls. Complementary DNA (cDNA) was generated from 1 μg RNA using Quantitect kit (Qiagen). Real Time PCR using Sybr Green (Qiagen) and Rotor Gene machines (Corbett) was used to determine levels of mRNA compared to GAPDH in samples for all isoforms of 14-3-3. See Table 1 for primer details.

Results 14-3-3ζ Mutant Mice Display Behavioural and Cognitive Defects 14-3-3 proteins are abundantly expressed in the developing and adult brain (Berg et al. *Nat Rev Neurosci* 2003; 4(9):752-762; Baxter et al. *Neuroscience* 2002; 109(1):5-14). To ascertain the role of 14-3-3ζ in neurodevelopment and brain function generated two knockout mouse lines were generated from embryonic stem cell clones containing retroviral gene-trap insertions within intron 1 or 2, termed 14-3-3 and 14-3-3ζ$^{Gt(OST390)Lex}$, respectively (FIG. 8; Lexicon Genetics). Quantitative RT-PCR and western blot on embryonic and adult brain tissue from heterozygous intercrosses confirmed that the gene trap vectors disrupted gene transcription and created null alleles (FIG. 9). These mutant lines are referred to as 14-3-3ζ$^{062+/-}$ and 14-3-3ζ$^{396+/-}$. Unlike deletions of other 14-3-3 isoforms (Su et al. *Proc Natl Acad Sci USA* 2011; 108(4):1555-1560), expression analysis further determined that removal of 14-3-3ζ is not compensated by increased expression of other 14-3-3 family members in mutant mice (FIG. 10). Inter crosses of 14-3-3ζ heterozygous mice from both strains gave rise to homozygous mutants in the predicted Mendelian ratio (WT 23%, Het 56%, Mut 21%; n=494, p<0.001) indicating that removal of the gene is not embryonic lethal. Initial inspection of mutant embryos and newborn mice suggested that development proceeded normally as they were morphologically indistinguishable from their littermates. However, by P14 mutant mice from both lines showed growth retardation and by P21 around 20% of mutant mice had died (WT 29%, Het 54%, Mut 17%; n=1619). The remaining mutant mice were smaller than WT littermates but had similar life expectancy (P100; WT 24.55±1.7 g, Mut 19.73 g±2.5 g). Mutant mice appeared outwardly normal and healthy with no differences in the olfactory test, visual test and wire-hang test.

To definitively analyse the association of 14-3-3ζ with neurological disorders and brain functions, a series of behavioural tests on mutant and control mice were completed. The response of 14-3-3ζ$^{062-/-}$ mice to an open field environment was first evaluated. Mutants showed a significant increase in distance travelled over the test period that was maintained throughout all testing ages (5, 10, 20 and 30 weeks), indicating that mutant mice are hyperactive (FIG. 1A). This effect was similar for both males and females with no sex bias (p>0.05).

The mouse's natural exploratory preference of novel objects rather than familiar objects was exploited to test recognition memory. Correct functioning of the perirhinal cortex in the medial lobe is essential for this task (Dere et al. 2006 supra; Sik et al. 2003 supra; Forwood et al. *Hippocampus* 2005; 15(3):347-355; Winters et al. *J Neurosci* 2005; 25(17):4243-4251). In the sample phase, mice spent an equal time exploring each identical object (14-3-3ζ$^{062+/+}$, 50.82±1.2%; 14-3-3ζ$^{062-/-}$ 49.18±1.2%). When presented with a familiar and new object, 14-3-3ζ$^{062-/-}$ mice exhibited significantly impaired novel object recognition compared to controls over the test period. Consistent with a lack of preference between the familiar and novel objects, 14-3-3ζ$^{062-/-}$ mice had a reduced discrimination index (time exploring novel object–time exploring familiar object/time exploring novel object+time exploring familiar object) indicating that they failed to retain new information (14-3-3ζ$^{062+/+}$, 0.1667±0.086 s; 14-3-3ζ$^{062-/-}$, -0.0569±0.047 s; p<0.05). Once again, there were no sex differences in either phase of testing (p>0.5). Notably, 14-3-3ζ$^{062-/-}$ mutants also demonstrated hyperactivity in the object recognition test with longer exploratory times in both phases of the trial (Sample phase, 14-3-3ζ$^{062+/+}$, 27.33±2.7 s; 14-3-3ζ$^{062-/-}$, 38.62±4.1 s; p<0.05: test phase, 14-3-3ζ$^{062+/+}$, 24.58±3.1 s; 14-3-3ζ$^{062-/-}$, 50.77±4.7 s; p<0.0001).

The elevated plus maze is widely used to test anxiety behaviour of rodents (Komada et al. 2008 supra; Wall et al. 2007 supra; Lister R G, *Psychopharmacology* (Berl) 1987; 92(2):180-185). When placed in such a test, 14-3-3ζ$^{062-/-}$ mice also demonstrated increased activity compared to wild type controls. 14-3-3ζ$^{062-/-}$ mice had 25.23±1.76 transitions between cross arms during a 5 min test period while 14-3-3ζ$^{062+/+}$ had 12.29±1.21 (p<0.0001). In addition, 14-3-3ζ$^{062-/-}$ mice spent significantly more time in the open arms (FIG. 1B: 114.8±11.5 s) compared to 14-3-3ζ$^{062+/+}$ mice (31.4 is 6.0 s, p<0.0001), entered them more often (14-3-3ζ$^{062+/+}$, 4.6+0.6; 14-3-3ζ$^{062-/-}$, 15.5±1.7, p<0.0001) and head dipped more, (14-3-3ζ$^{062+/+}$ 19.6±1.5; 14-3-3ζ$^{062-/-}$; 33.4±2.4 p=0.0041) suggesting that they had lower levels of anxiety.

Figure 11:
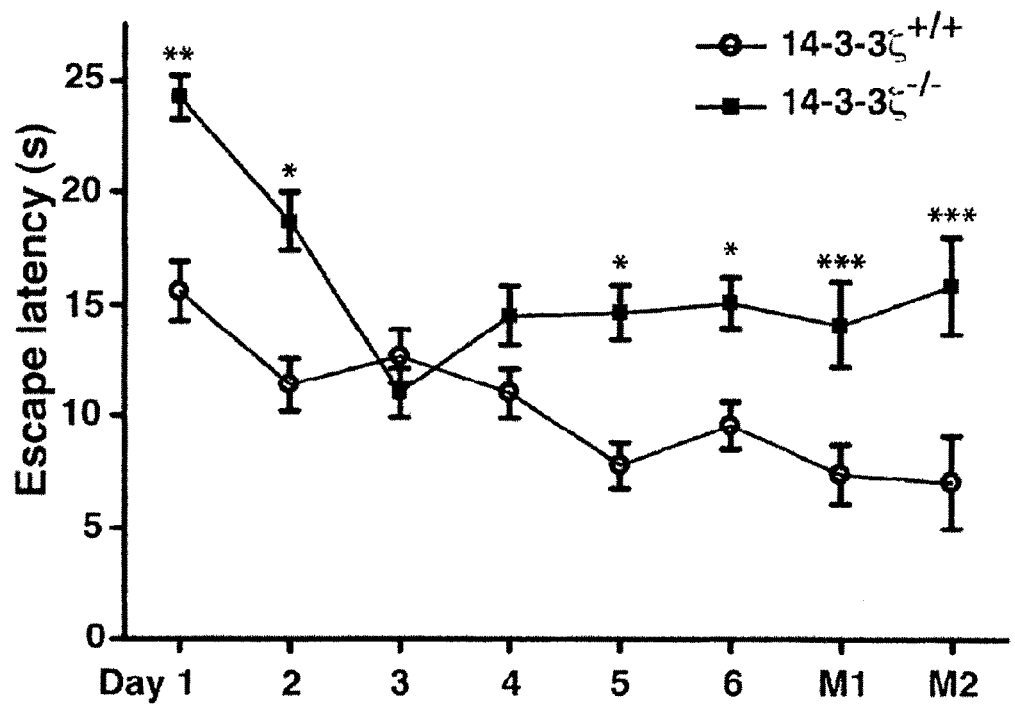
FIG. 11: 14-3-3$\zeta$-deficient mice display cognitive dysfunction in learning and memory. 14-3-3$\zeta^{062-/-}$ mice (open circles; n=12) have lower capacity than 14-3-3$\zeta^{062+/+}$ mice (closed squares; n=12) for both spatial learning (Day 1-6) and memory in a cross maze escape task test. 14-3-3$\zeta^{062-/-}$ mice take longer to reach the escape platform throughout the training period and during the memory test phase (M1 and M2). Data from male and female mice is pooled. Error bars are presented as mean±SEM. *, p<0.05; , p<0.01; *, p<0.001.

Spatial working memory-dependent learning was examined using a cross maze escape task (Summers et al. 2006 supra). Appropriate signalling between the hippocampus and prefrontal cortex are a prerequisite for acquisition of this task. Mice were trained over 6 days to identify the correct arm of a cross maze containing a submerged escape platform. Each arm of the cross maze was denoted by a novel visual cue throughout the experiment. Although some 14-3-3ζ$^{062-/-}$ mice learnt to identify the correct arm, they showed increased latency in reaching the platform over the course of the acquisition period (FIG. 11; $\chi^2$ (5)=29.8808; p<0.0001) and had significantly decreased arm choice accuracy (FIG. 1C: IRR=0.52; p<0.0001). Their ability to remember the correct cross-arm was then tested by resting them for 14 days or 28 days post acquisition followed by re-testing in the escape platform water maze (M1 and M2, respectively). In comparison to the learning phase, 14-3-3ζ$^{062+/+}$ mice showed no change in escape latency (HR=1.18, p=0.383), whilst 14-3-3ζ$^{062-/-}$ demonstrated significantly increased escape latency (HR=2.98, p<0.0001). Consistent with dysfunction in hippocampus-dependent memory, mutant mice also had a significant decrease in arm choice accuracy (FIG. 1C: IRR=0.231; p<0.0001). All cognitive defects were independent of sex.

Figure 12:
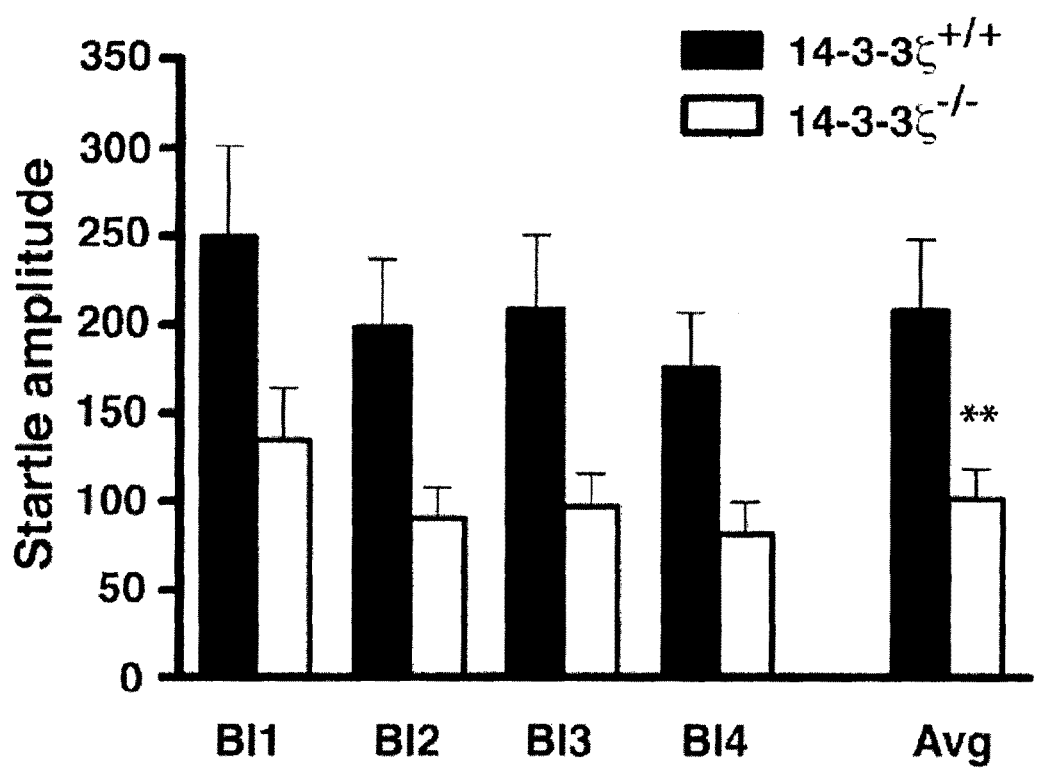
FIG. 12: 14-3-3$\zeta$-deficient mice display reduced startle reflex. Startle amplitude of 14-3-3$\zeta^{062-/-}$ mice (open bar; n=13) is lower than 14-3-3$\zeta^{062+/+}$ mice (closed bars; n=14) over four pulse-alone blocks of 115 dB. The average (Avg) startle from all blocks is also shown. **, <0.05.

Defects in sensorimotor gating are an endophenotype of neuropsychiatric disorders such as schizophrenia and related disorders. Appropriate signalling in the hippocampus and other brain regions are essential for this filtering mechanism. To determine if 14-3-3ζ mutant mice have abnormal sensorimotor gating, prepulse inhibition (PPI) of the acoustic startle reflex was assessed. It was found that 14-3-3ζ$^{062-/-}$ mice had a significantly lower PPI (FIG. 1D: main effect of genotype F(1,20)=5.89, p=0.025) and startle (FIG. 12: F(1, 20)=5.87, p=0.023) compared to 14-3-3ζ$^{062+/+}$ mice. Increasing levels of prepulse intensities caused similar increases in PPI in WT and mutant mice (FIG. 1D). Overall, startle amplitudes were reduced in mutant mice but startle habituation was normal (FIG. 12).

14-3-3ζ, is Expressed in Hippocampal Neurons to Control Lamination

Figure 2:
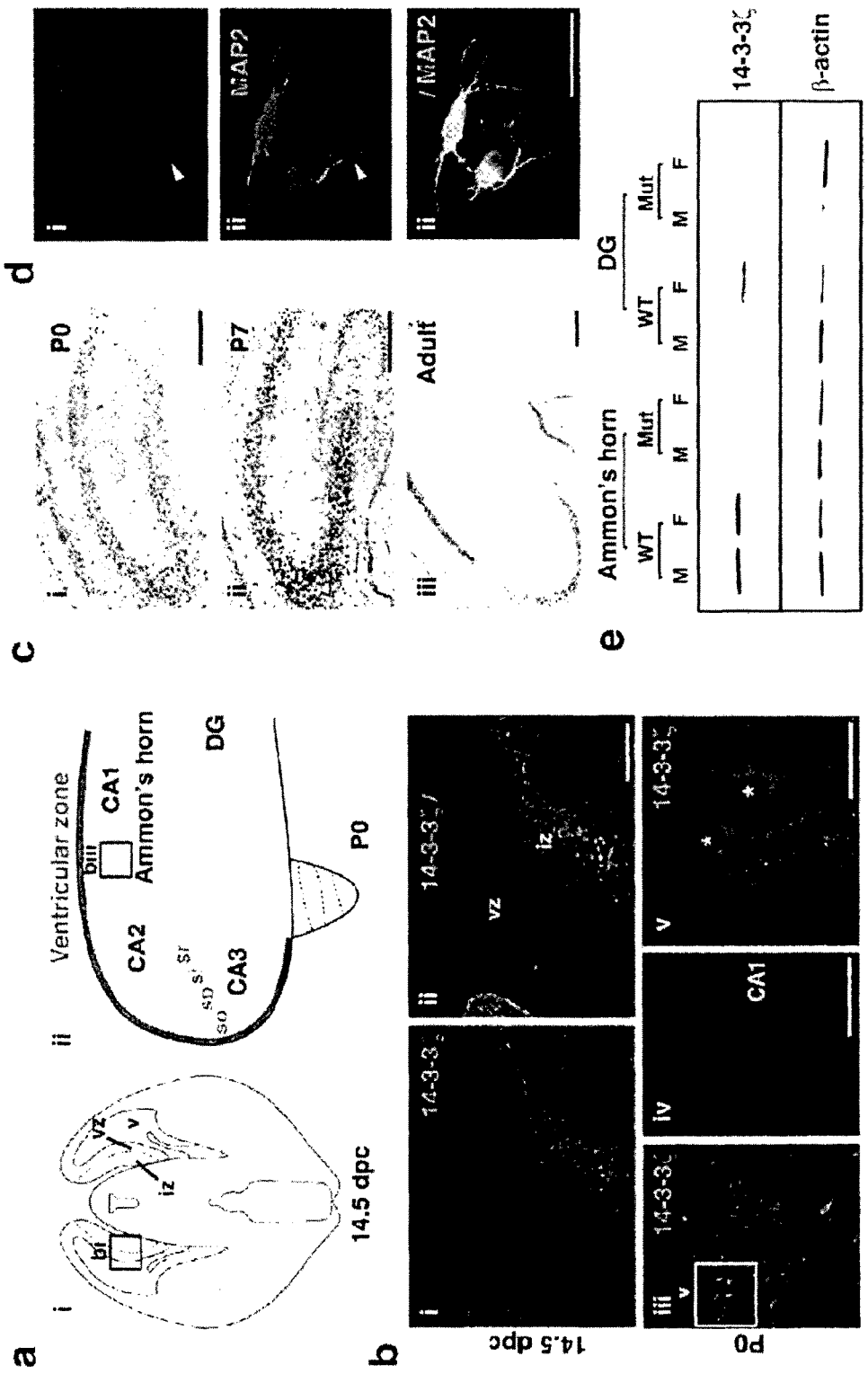
FIG. 2. 14-3-3ζ is expressed in the pyramidal cells of Ammon's horn and granule neurons of the dentate gyrus. (a) (i) Schematic representation of a coronal section through a 14.5 dpc embryonic mouse brain depicting the different regions of the hippocampus. V, ventricle; IZ, intermediate zone; VZ, ventricular zone. (ii) Schematic representation of a coronal section through P0 mouse hippocampus. Neurons from the hippocampal primordium originate from the ventricular neuroepithelium (light blue) and neuroepithelium adjacent to the fimbria (dark blue). The three subfields containing the pyramidal neurons of the cornu ammonis (CA1-3) that compose Ammon's horn and its layers (so, stratum oriens; sp. stratum pyramidale; sl, stratum lucidum; sr, stratum radiatum) are depicted in relation to positioning of granular neurons in the dentate gyrus (DG). (b) (i-ii) 14-3-3ζ immunoreactivity was detected in the intermediate zone of the 14.5 dpc developing hippocampus. (iii-iv) At P0, 14-3-3ζ-positive neurons are located in the pyramidal cell layer. (v) Higher magnification of the pyramidal neurons (asterisks) shows that 14-3-3ζ has a punctate cytoplasmic localisation. (c) X-gal staining showing the endogenous expression of 14-3-3ζ in P0, P7 and adult 14-3-3ζ$^{062+/-}$ hippocampi. The high level of 14-3-3ζ-lacZ expression is evident in pyramidal and granular neurons. (d) Hippocampal neuronal culture. (i) 14-3-3ζ staining with EB1 (red). (ii) MAP2 positive (green) hippocampal neurons. (iii) Overlay of 14-3-3ζ and MAP2 highlights the co-expression in MAP2 positive neurites (arrow). (e) 14-3-3ζ protein (27 kDa) is expressed in Ammon's horn and dentate gyrus of the WT mice. Western blot of lysates from adult WT and 14-3-3ζ$^{062-/-}$ mice were immunoblotted and probed with antibody to 14-3-3ζ (EB1). Anti-(3-actin (42 kDa) antibody was used as a loading control. Scale bars=100 μm (bi-iv; c; di-iii), 25 μm (bv).
Figure 13:
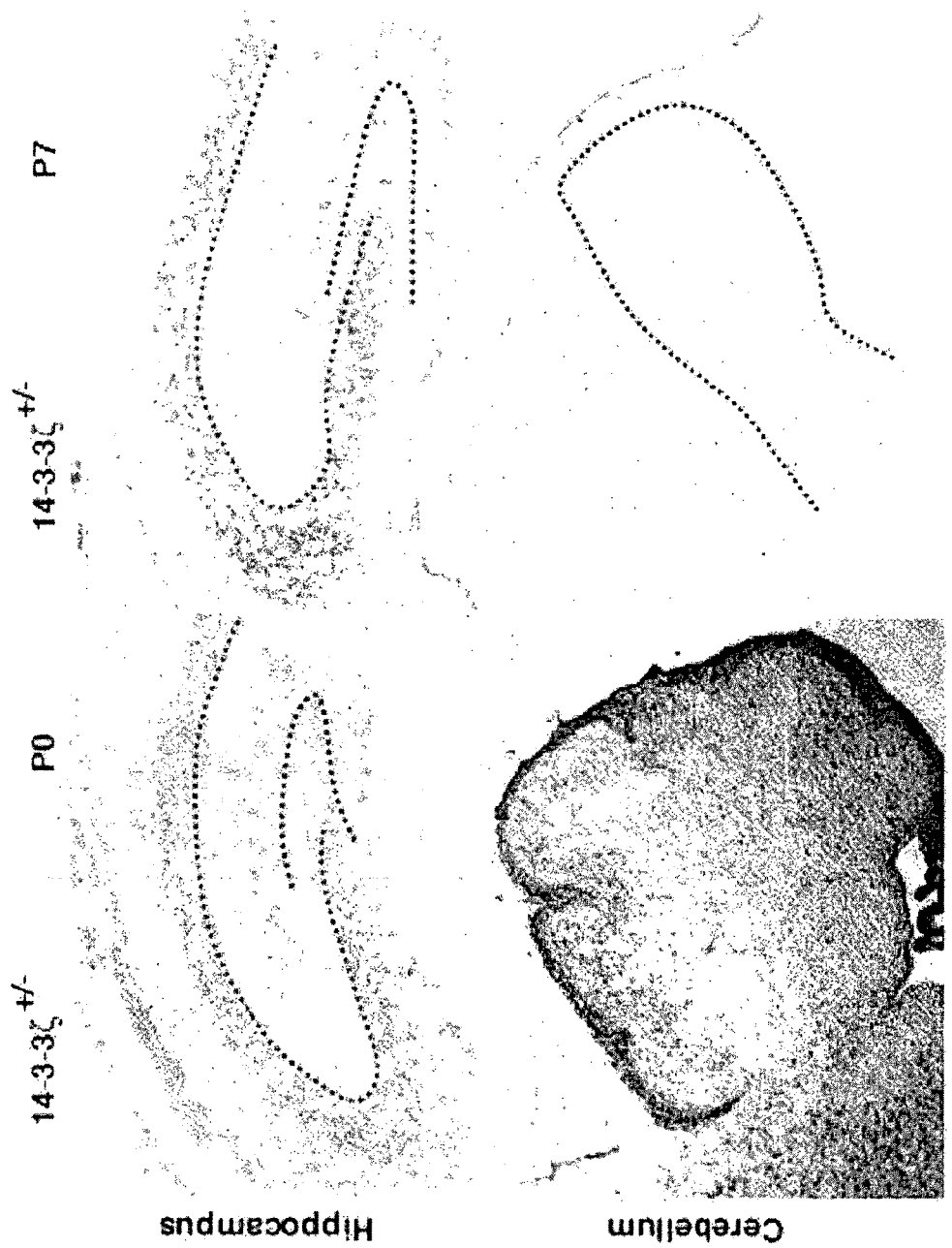
FIG. 13: 14-3-3$\zeta$ expression is maintained in hippocampal neurons. X-gal staining showing the endogenous expression of 14-3-3$\zeta$ in P0 and P7 14-3-3$\zeta^{062+/-}$ hippocampus and cerebellum. The high level of 14-3-3$\zeta$-lacZ expression in the hippocampus is evident in both the pyramidal neurons of the Ammon's horn and the mature dentate neurons but not in the cerebellum post-birth. Scale bar=25 μm.

To determine if the cognitive and behavioural deficits arise from neurodevelopmental defects of the hippocampus, the role of 14-3-3ζ in neuronal development was analysed. Hippocampal neurons derive from the neuroepithelium along the ventricular zone (NEv) and from a restricted area of neuroepithelium adjacent to the fimbria (NEf) (Nakahira et al. *J Comp Neurol* 2005; 483(3):329-340) (FIG. 2A). At 14.5 dpc 14-3-3ζ immunostaining was detected in migrating hippocampal neurons within the intermediate zone, but not in their neuroepithelial precursors (FIG. 2Bi). By P0 14-3-3ζ immunostaining was also detected in pyramidal cells of the hippocampal proper/cornu ammonis (CA) (FIG. 2B iii). Taking advantage of the Beta-geo transgene within the gene trap vectors of the 14-3-3ζ mouse lines endogenous expression of 14-3-3ζ with B-galactosidase staining in heterozygous mice was monitored. Consistent with immunostaining, expression of 14-3-3ζ at the transcript level in migrating CA neurons was identified. In addition, expression within CA and DG neurons was detected into late adulthood (FIG. 2C). Unexpectedly, however, 14-3-3ζ was undetectable in other regions of brain, such as the cerebellum, after early post natal stages (FIG. 13). Expression within CA and DG neurons was confirmed by western blot of protein extracted from microdissected adult hippocampi (FIG. 2D). This also confirmed complete removal of the protein from these brain regions of 14-3-3ζ062−/− mice. Finally, after 10 days in vitro (DIV), hippocampal MAP2 positive neuronal cultures also showed punctate immunocytostaining for 14-3-3ζ within the cell body and axon/dendrites (FIG. 2E).

Figure 3:
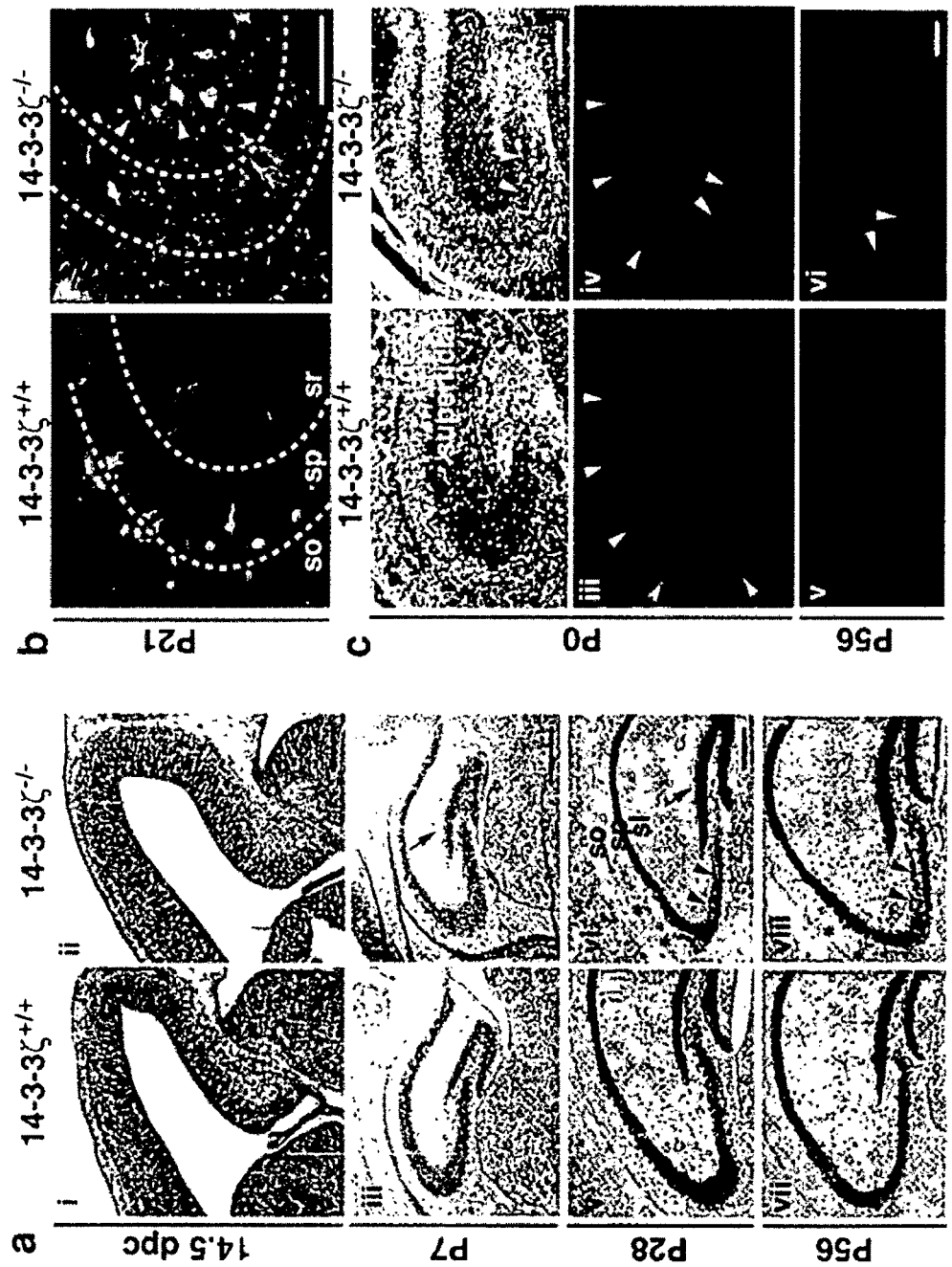
FIG. 3: 14-3-3-ζ-deficient mice displayed lamination defects of the hippocampus. (a) Nissl staining shows the hippocampal development of WT and 14-3-3ζ$^{062-/-}$ mice from 14.5 dpc until postnatal-day-56 (P56). Hippocampal cells are dispersed in the stratum pyramidale (sp) of the 14-3-3ζ$^{062-/-}$ mice (iv, vi, viii). Arrowheads highlight the duplicated layer of the hippocampal pyramidal neurons in stratum radiatum (sr). Asterisks highlight the ectopically positioned pyramidal cells in the stratum oriens (so). Arrows indicate the loosely arranged granule neurons in the dentate gyrus. (b) Thy1-YFP transgene expression introduced in to the 14-3-3ζ$^{062}$ background revealed severe disorganization of hippocampal pyramidal neurons in 14-3-3ζ$^{062-/-}$ mice. Blue, DAPI; green, Thy1 expression (c) Coronal sections of the hippocampus obtained from P0 (i-iv) and P56 (v-vi) mice of the indicated genotype. The deeper stratum pyramidale is populated by NeuN-positive pyramidal cells in WT hippocampi (iii, yellow arrowheads) forming a uniform mature zone from CA1 to CA3. In 14-3-3ζ$^{062-/-}$ hippocampi, the maturation zone was less uniform with some NeuN-positive mature pyramidal cells ectopically positioned in both the deeper zone (yellow arrowheads) and superficial zone (white arrowheads) of the stratum pyramidale in CA3. In P56 14-3-3ζ$^{062-/-}$ mice, immunostaining for NeuN highlighted pyramidal cells in the duplicated CA3 subfields indicating that ectopic cells achieved maturation (vi). Scale bars: 100 um.
Figure 14:
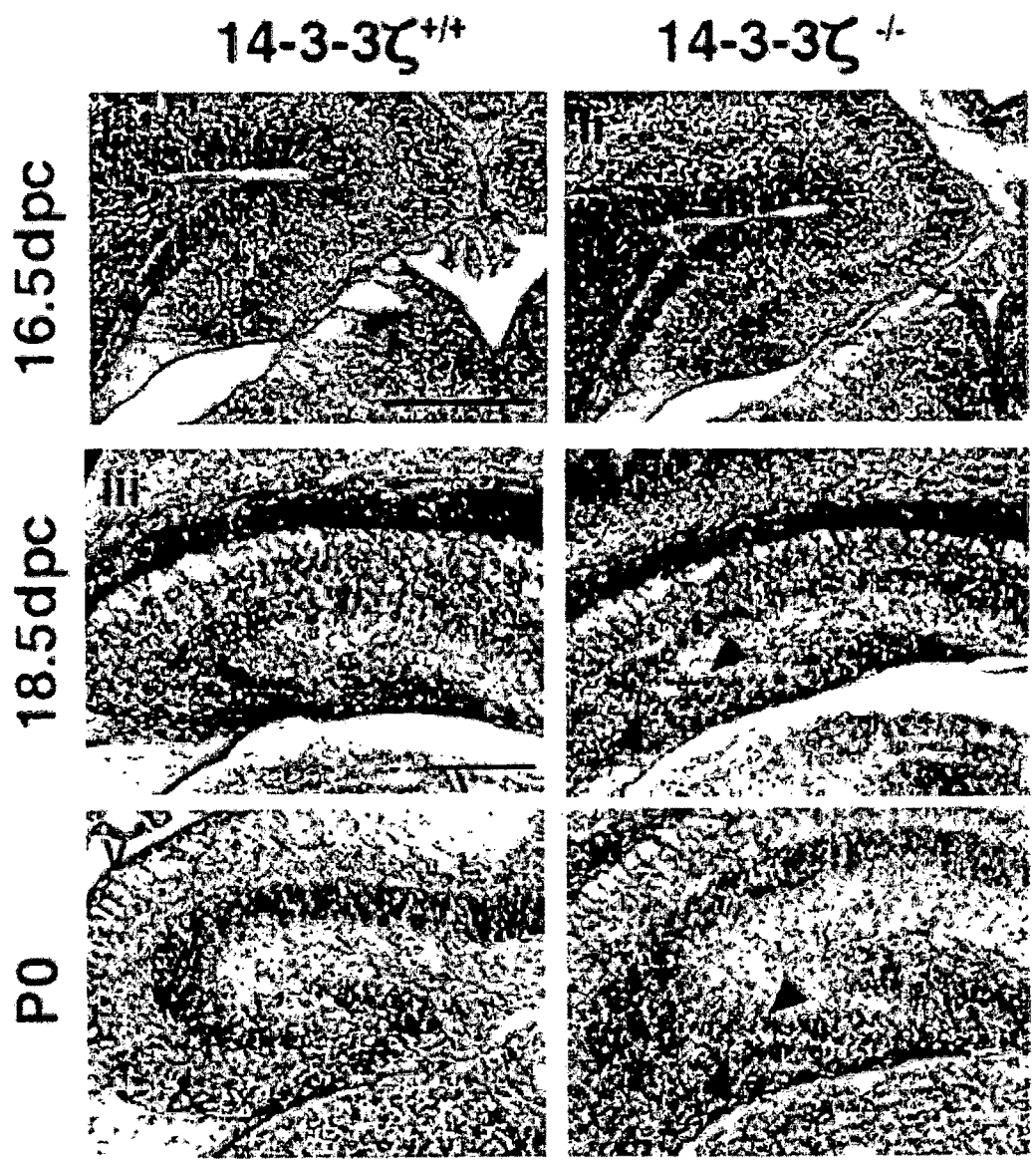
FIG. 14. Hippocampal lamination defects in 14-3-3ζ-deficient mice. Nissl staining shows the hippocampal development of WT (i, iii, v) and 14-3-3ζ$^{062-/-}$ (ii, iv, vi) mice from 14.5 dpc until birth (P0). Hippocampal cells were dispersed in the stratum pyramidale (sp) of the 14-3-3ζ$^{062-/-}$ mice. Arrowheads highlight the duplicated layer of the hippocampal pyramidal neurons in stratum radiatum (sr). Asterisks highlight the ectopically positioned pyramidal cells in the stratum oriens (so). Scale bar 25 μm.

As 14-3-3ζ is expressed in hippocampal neurons we next examined if CA and DG neurons were examined to determine if they are positioned correctly in adult and embryonic mutants. Nissl-staining of 14-3-3ζ$^{062-/-}$ mice revealed developmental defects first noticeable prior to hippocampal maturation (5/5 at P0, 4/4 at P7, 2/2 at P28 and 2/2 at P56; FIG. 3A and FIG. 14). Specifically, pyramidal neurons were ectopically positioned in the stratum radiatum and stratum oriens in addition to their usual resting place of the stratum pyramidale. Within the CA3 subfield, pyramidal neurons split in to a bilaminar stratum instead of a single cell layer. Dentate granule neurons were also diffusely packed in the 14-3-3ζ$^{062-/-}$ mice compared with 14-3-3ζ$^{062+/+}$ littermates. Consistent with Nissl staining, analysis of hippocampal organization in thy1-YFP mice also revealed a disrupted laminar organization (FIG. 3B).

Figure 15:
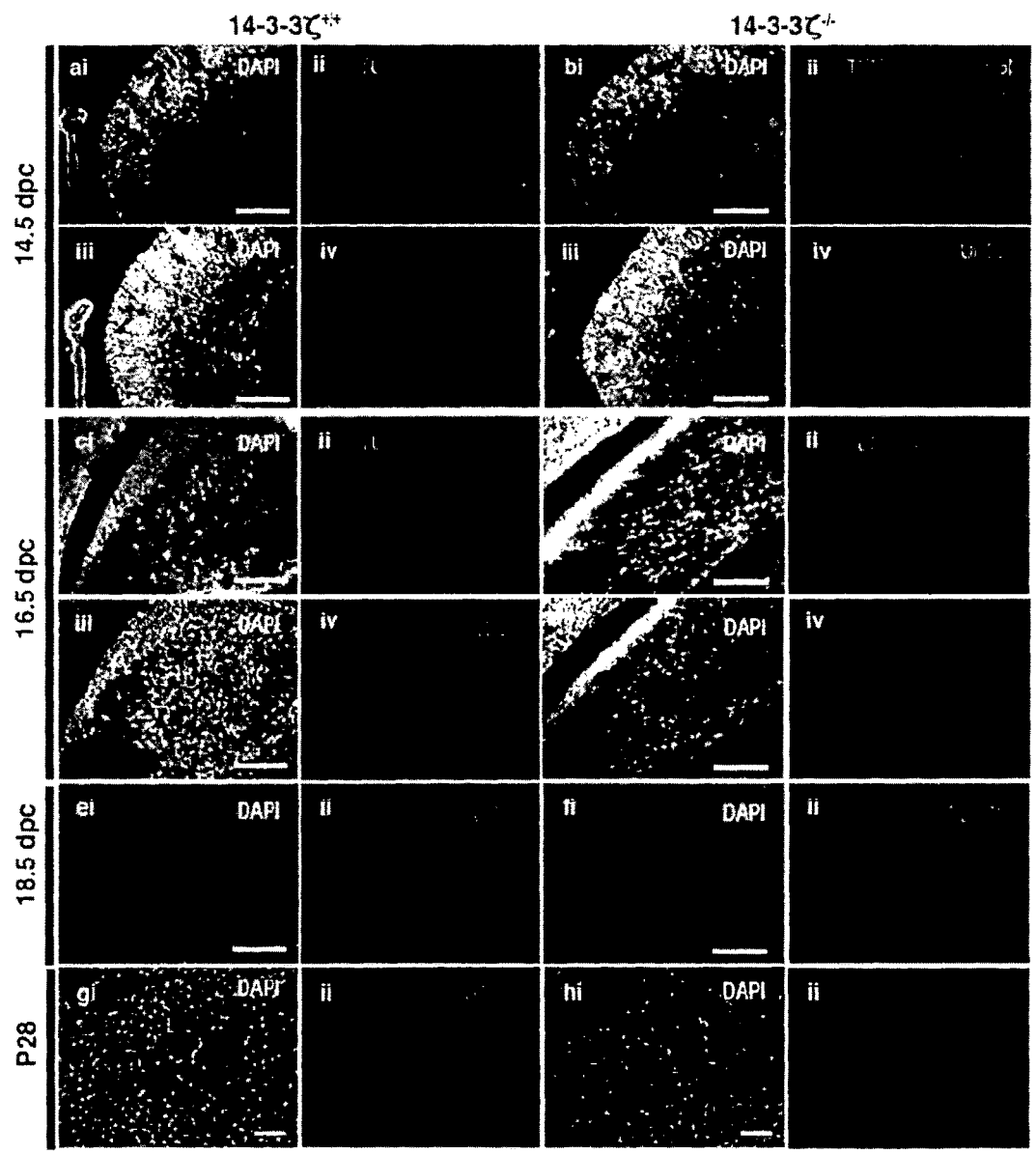
FIG. 15: Mispositioned neurons in 14-3-3ζ-deficient mice survive into adulthood. Apoptotic cells in hippocampal primordium (a-f) and mature hippocampi (g-h). No increase in fragmented, apoptotic cell nuclei (as shown in the green TUNEL positive cells in aii and bii) were detected 14-3-3ζ$^{-/-}$ hippocampi. Scale bar=100 μm.

Consideration was then directed to whether ectopically positioned pyramidal cells developed into mature neurons. In all 14-3-3ζ$^{062-/-}$ hippocampi (4/4 pups) ectopic cells were positive for the neuronal marker NeuN (FIG. 3C). Rather than positioning themselves in the deep molecular layer, neurons also matured in the superficial layer of CA3. Together, this data infers that mispositioned cells in the hippocampus form functional pyramidal and granular neurons. Additionally, TUNEL staining of hippocampi from embryonic, early postnatal and adult mice showed no apparent differences between genotypes (FIG. 15) suggesting that lack of 14-3-3ζ does not affect neuronal viability.

14-3-3ζ-Deficient Mice Display Hippocampal Neuronal Migration Defects

Figure 4:
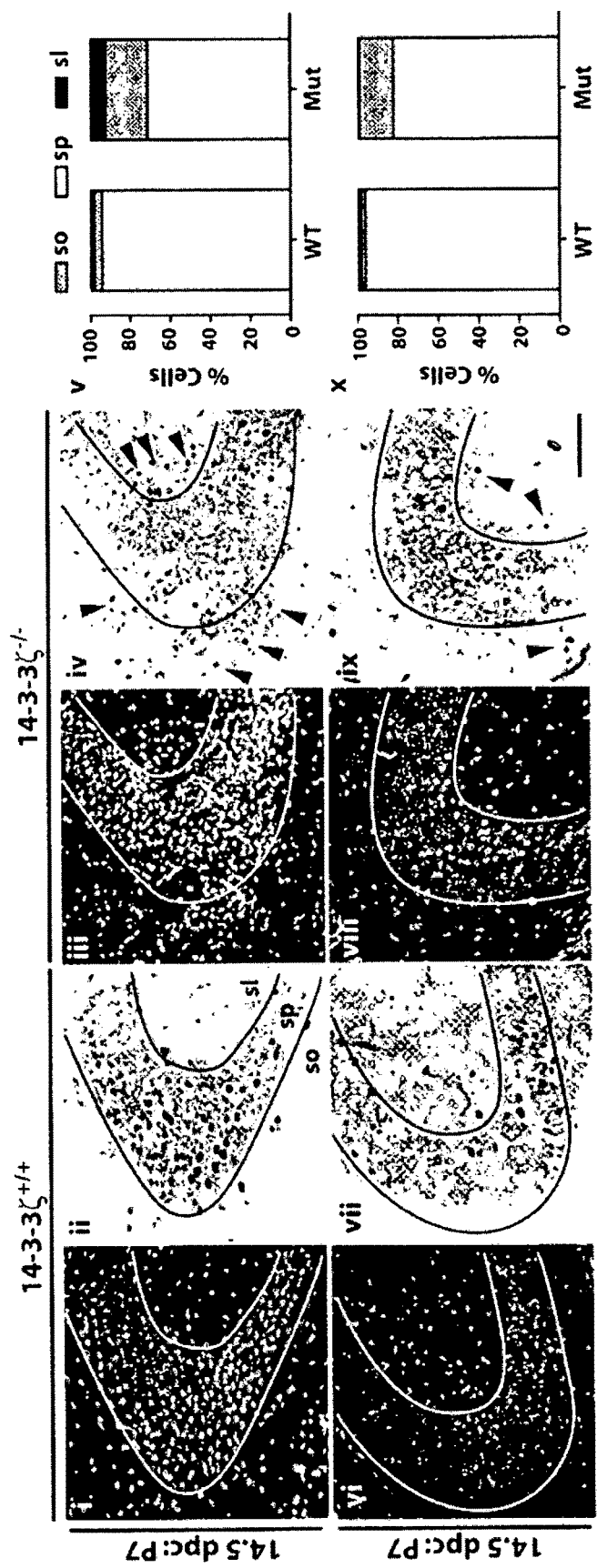
FIG. 4: BrdU-pulse-chase analysis indicates neuronal migration defect in 14-3-3ζ-deficient mice. BrdU-pulse-chase analysis at 14.5 dpc:P7 (i-v) and 16.5 dpc:P7 (vi-x) demonstrates that the BrdU-positive cells (black) locate within the stratum pyramidale (sp) in the CA3 subfield of WT hippocampi (ii & vii). (v) Graph summarizes the percentage of the ectopic hippocampal neurons at 14.5 dpc:P7. BrdU-labelled cells of 14-3-3$\zeta^{062-/-}$ mice were ectopically positioned. Neurons were stalled in the stratum oriens (so), or migrated beyond the stratum pyramidale and into the stratum lucidum (sl) (arrowheads in iv & ix). (x) Graph summarizes the percentage of the ectopic hippocampal neurons at 16.5 dpc:P7. Scale bars: 100 μm

The expression of 14-3-3ζ within the intermediate zone at 14.5 dpc and the presence of mature neurons in the superficial layer at P0 raised the possibility that the aberrant laminar structure may arise from erroneous migration. To visualize hippocampal neuron migration, BrdU birthdating was completed by injecting BrdU into pregnant dams from heterozygous 14-3-3ζ$^{062}$ crosses at 14.5 dpc and 16.5 dpc. 14-3-3ζ$^{062+/+}$ and 14-3-3ζ$^{062-/-}$ pups were collected at P7 and BrdU-retaining cells were identified in coronal sections. Sections were counterstained with DAPI to identify separate layers of the hippocampus. BrdU-retaining cells were counted from 10 μm sections using 5 mice of each genotype and the relative percentage in each layer was quantified. Both injection time points show that nearly all neurons born in the ventricular zone at 14.5 dpc or 16.5 dpc migrate in to the stratum pyramidale of the CA in control mice (FIG. 4). Strikingly, however, a significant percentage of BrdU-retaining cells were identified outside of the stratum pyramidale in 14-3-3ζ$^{062-/-}$ mice. Failure of neurons to migrate from their birthplace or to stop within their correct layer therefore gives rise to the duplicated stratum pyramidale in the 14-3-3ζ$^{062-/-}$ hippocampus.

Figure 5:
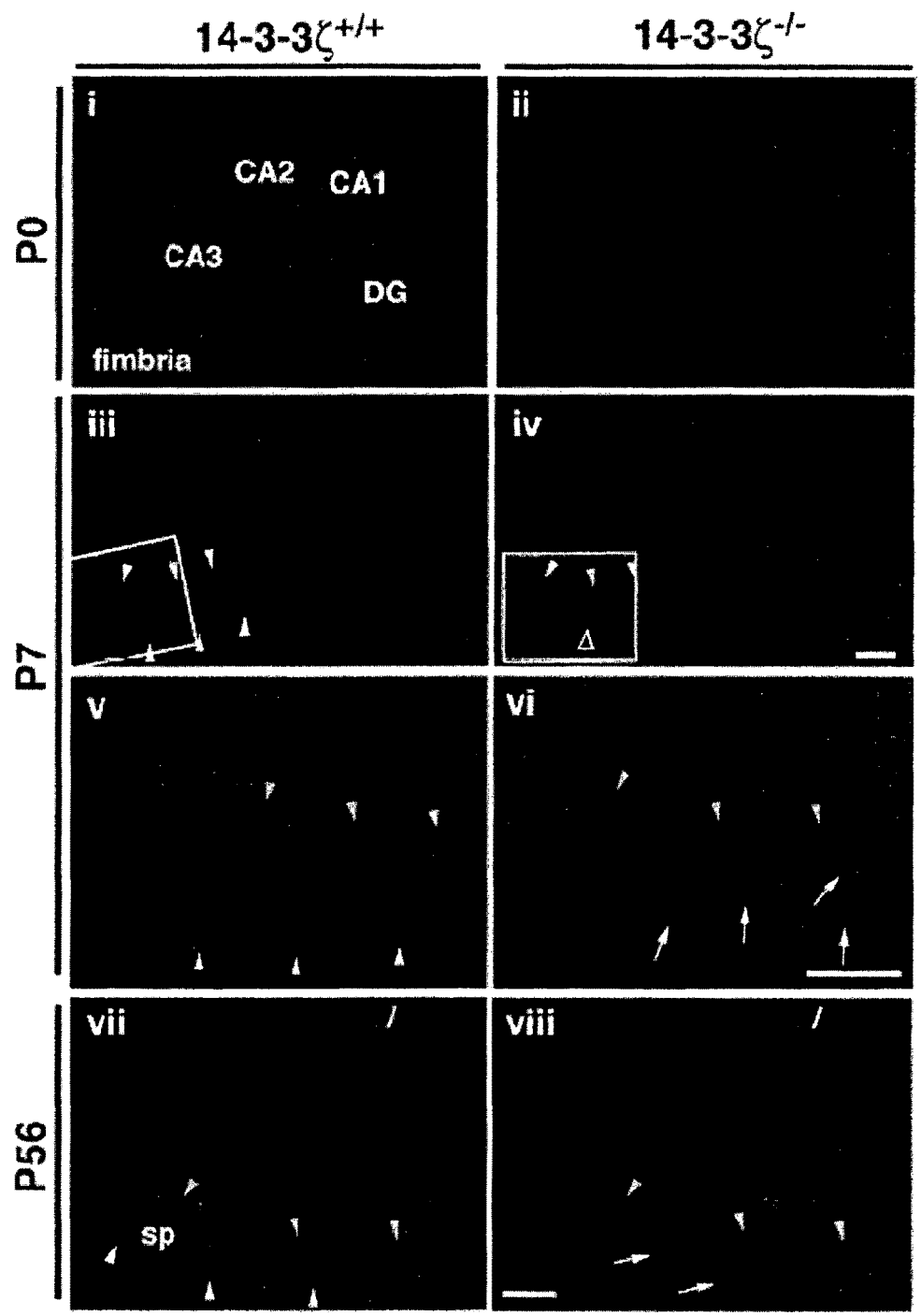
FIG. 5: Abnormal mossy fibre pathways in 14-3-3$\zeta$-deficient mice. Calbindin immunostaining of the infrapyramidal (IPMF, yellow arrowheads) and the suprapyramidal (SPMF, white arrowheads) mossy fibre trajectories in 14-3-3$\zeta^{062+/+}$ (i, iii, v and vii) and 14-3-3$\zeta^{062-/-}$ (ii, iv, vi and viii) mice. Similar to WT controls, 14-3-3$\zeta^{062-/-}$ deficient neurites initially bifurcate into the SPMF and IPMF branches after navigating away from the dentate gyrus (DG). However, the IPMF branch of 14-3-3$\zeta^{062-/-}$ mice navigated aberrantly among the pyramidal cell somata (sp. white arrows). In, addition, the diffuse SPMF branch of 14-3-3$\zeta^{062-/-}$ mice invaded the duplicated pyramidal cell layer in CA3. Scale bars=100 μm.

Functional Disrupted Mossyfibre Circuit and Aberrant Synaptic Terminals in Pyramidal Cells in 14-3-3ζ-Deficient Mice Communication between the CA3 pyramidal neurons and DG granule cells is achieved through precise axonal navigation and synaptic targeting. The issue of whether misaligned pyramidal neurons affected the hippocampal circuit was assessed by performing immunohistochemical staining with anti-calbindin in P0, P7 and P56 hippocampi. In control mice, mossy fibres sprouted from the somata of the granule cells and bifurcated into infrapyramidal mossy-fibre (IPMF) and suprapyramidal mossy fibre (SPMF) tracts spanning the stratum pyramidale of CA3 (FIG. 5). In 14-3-3ζ$^{062-/-}$ mice the IPMF tract navigated along the apical surface of CA3 pyramidal neurons, however, the SPMF tract was misrouted amongst the CA3 neurons.

Figure 6:
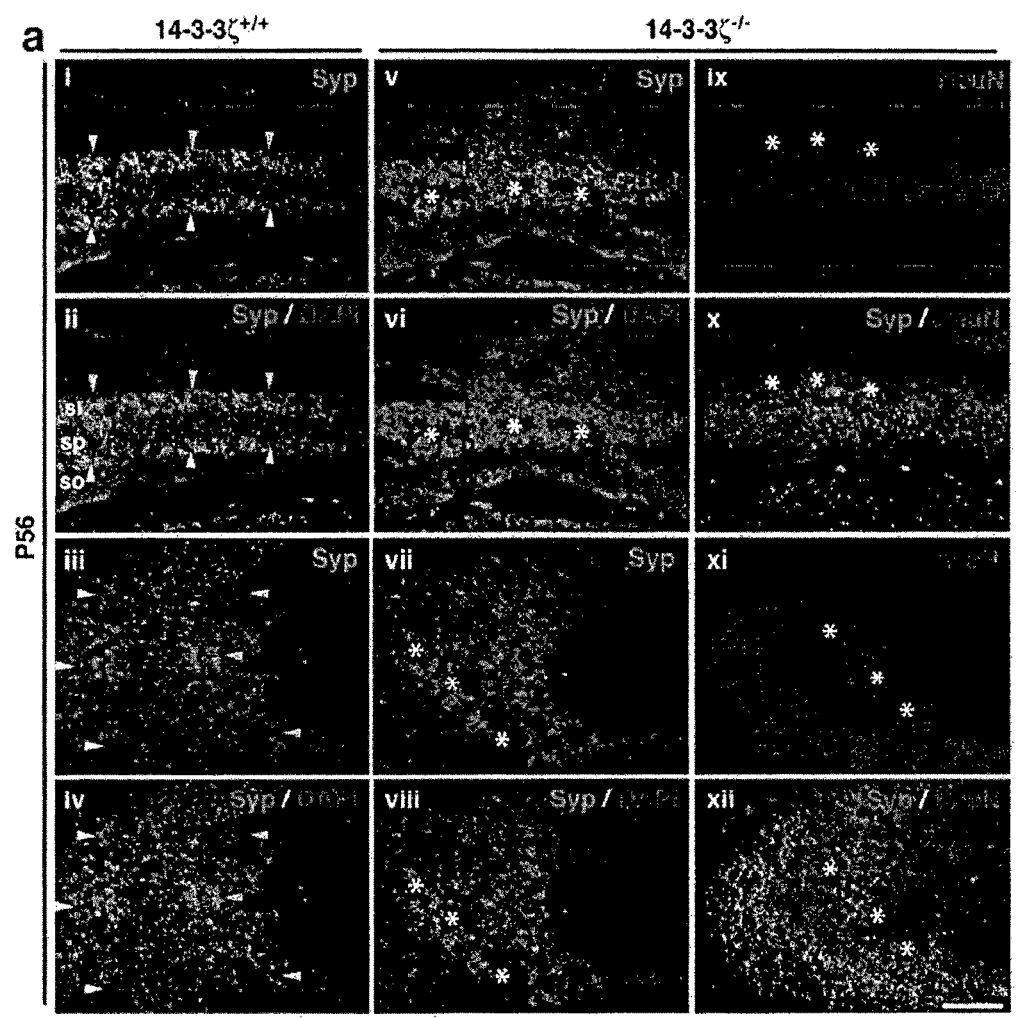
FIG. 6: Functional synaptic connection between ectopic CA3 pyramidal cells and misrouted mossy fibres. (a) (i-iv) Hippocampal sections from P56 14-3-3$\zeta^{062+/+}$ mice stained with antibodies to synaptophysin (Syp) show immunoreactivity in both the IPMF (white arrowheads) and SPMF (yellow arrowheads). Syp staining is located in both the stratum oriens (so) and stratum lucid=(sl), surrounding the pyramidal somata of CA3. (v-viii) Syp staining of hippocampal sections from 14-3-3$\zeta^{062-/-}$ mice reveals that the mossy fibres navigating abnormally within the stratum pyramidale of CA3 (asterisks, v, vii) form functional synapses. (ix-xii) Ectopic mature CA3 pyramidal cells (stained by NeuN; depicted with asterisks) communicate with the synaptic protein (Syp, green) from the misrouted mossy fibres. Scale bars=100 μm. (b) Golgi stain reveals the dendritic arborization of the pyramidal cells of WT or 14-3-3$\zeta^{062-/-}$ adult mice (P35). A set of thorny excrescences, indicating the contact points with the misrouted mossy fibre synaptic boutons (MFB, bevelled line), is located on the apical proximal dendrites of CA3 pyramidal cells in WT neurons. Two sets of thorny excrescences are located on the apical dendritic tree in 14-3-3$\zeta^{062-/-}$ mice, one at the proximal apical dendrites and the other in the distal dendritic branches (*). (c) Schematic diagram depicts the misrouted mossy fibre trajectories and aberrant synaptic points of mossy fibre boutons communicating to the ectopic CA3 pyramidal cells in 14-3-3$\zeta^{062-/-}$ mice as compared to WT hippocampi.
Figure 6:
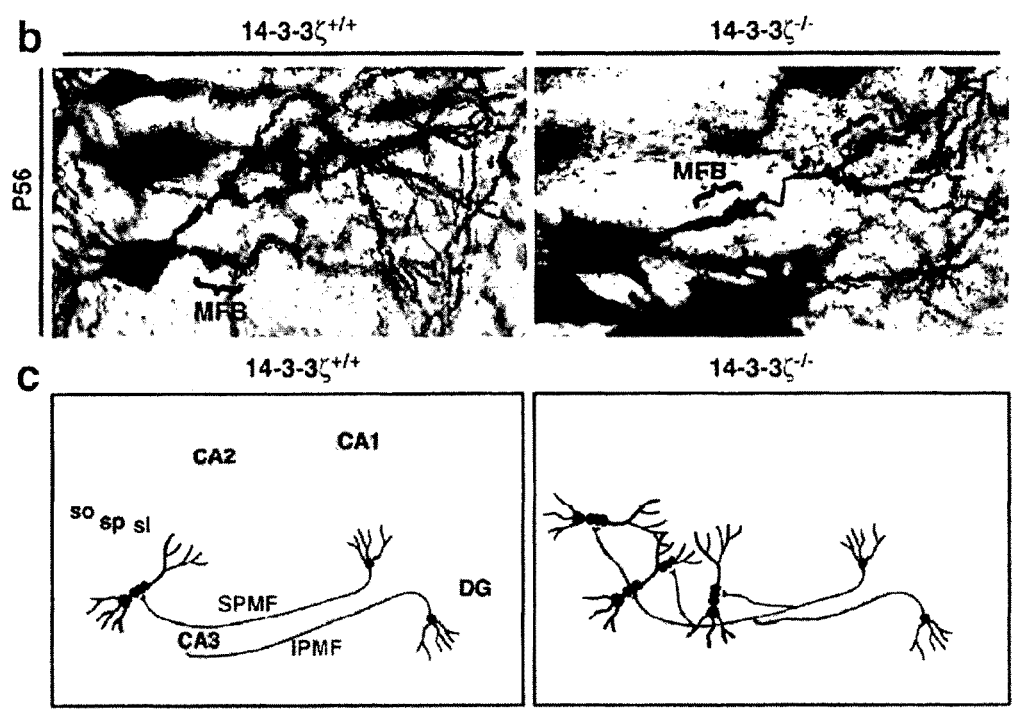

To determine whether DG granular cells synapsed on their CA target cells, anti-synaptophysin was used to identify presynapses in both the IPMF and SPMF of the CA3 subfield in control animals. In 14-3-3ζ$^{062-/-}$ mice, misrouted axons also formed aberrant synapses within the stratum pyramidale (FIG. 6). Visualisation of synaptic boutons by golgi stain further revealed notable differences in synapse formation in CA3. In control animals large spine excrescences on the proximal region of the apical dendrites were followed by fine-calibre dendritic branches. In pyramidal neurons of 14-3-3ζ$^{062-/-}$ mice the dendritic, tree appeared to have similar numbers of branch points but had thorny excrescences from the misrouted mossy fibre tracts on both proximal and distal apical dendrites of all mice examined.

Figure 7:
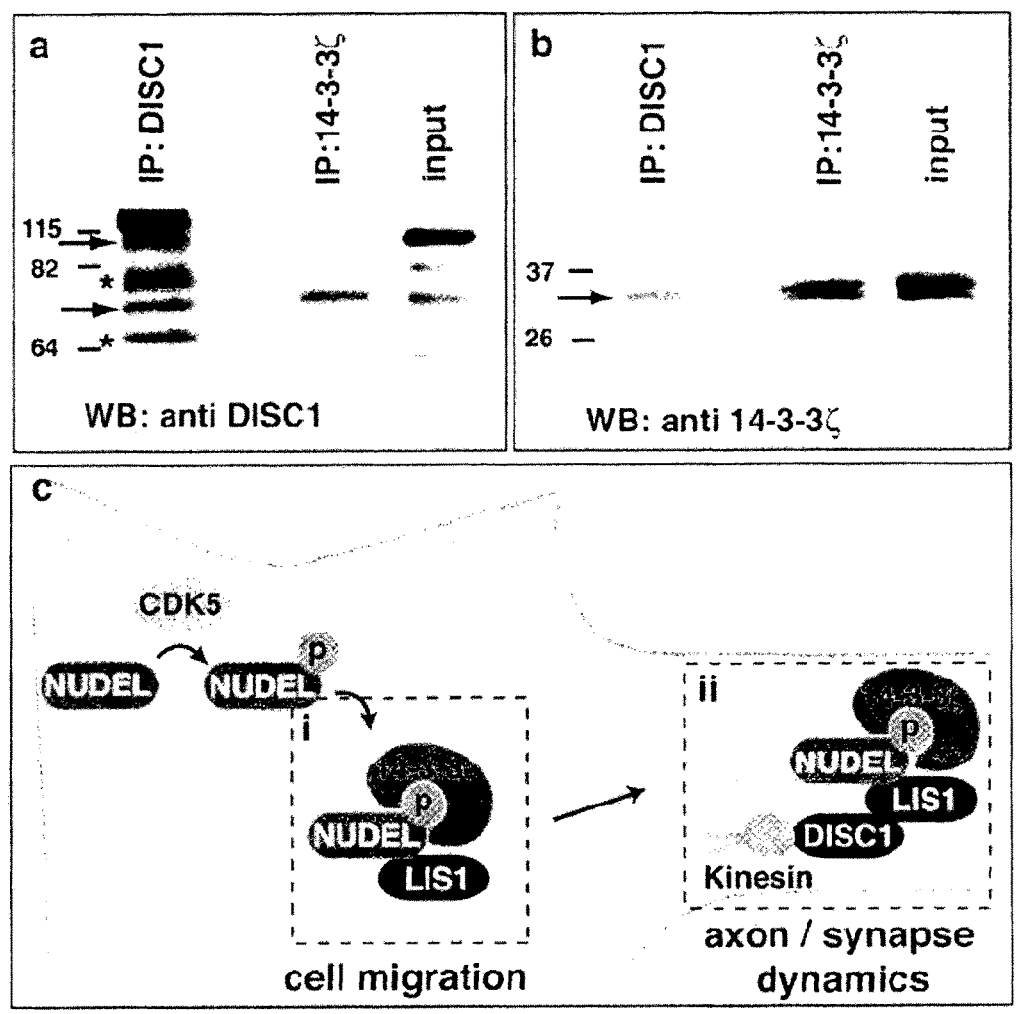
FIG. 7: 14-3-3$\zeta$ interacts with DISC1 to control neuronal development. (a-b). Equal amounts of lysate from P7 mouse brains were immunoprecipitated with anti-DISC1 antibodies or anti-14-3-3 antibodies and immunoblotted with DISC1 (a), or EB1 purified antisera to recognize 14-3-3$\zeta$ (b). The relative expression levels of DISC1 isoforms and 14-3-3$\zeta$ from 5% of total cell lysate (input) used for co-immunoprecipitation were also determined by direct immunoblotting. Arrows indicate the major 100 kDa and 75 kDa bands of DISC1 (a) and 27 kDa band representing 14-3-3$\zeta$ (b). Asterisk represents background IgG bands from immunoprecipitation. (c) Schematic representation of the role of 14-3-3$\zeta$ in neuronal migration and axonal growth. (i) 14-3-3$\zeta$ binds CDK5 phosphorylated Ndel1 to promote interaction with LIS1 and thereby promote neuronal migration. (ii) 14-3-3$\zeta$ is also present in the LIS1/Ndel1/DISC1 complex to control axonal growth dynamics.

To identify the molecular pathways employed by 14-3-3ζ to coordinate neuronal migration and axonal pathfinding co-immunoprecipitation experiments were performed on whole brain extracts from P7 mice. It was found that 14-3-3ζ could be co-immunoprecipitated with an antibody raised to the C-terminus of DISC1. Vice versa, it was also found that DISC1 could be co-immunoprecipitated with an antibody recognising 14-3-3ζ (FIG. 7). Surprisingly, the data indicate that 14-3-3ζ interacts specifically with the 75 kDa form of DISC1 rather than the 100 kDa full length protein, indicating that DISC1 functions in an isoform specific manner in neurodevelopment.

Example 2

Figure 16:
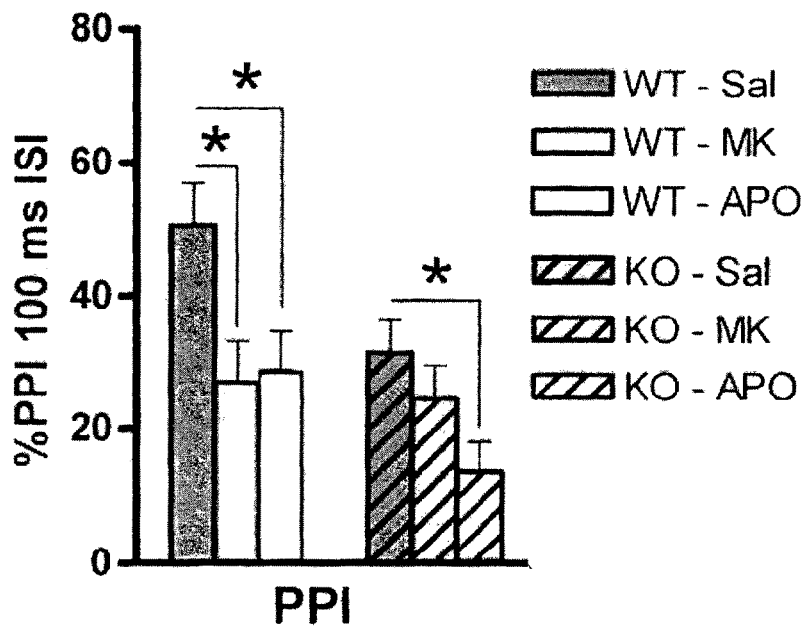
FIG. 16: 14-3-3ζ controls glutamataregic pathways to mediate sensorimotor gating. Compared to 14-3-3ζ$^{062+/+}$ mice (grey bar; n=11; 5 male and 6 female) the 14-3-3ζ$^{062-/-}$ mice (grey hashed bar; n=11; 5 male and 6 female) have reduced PPI with a prepulse (PP) of 16 dB over the 70 dB baseline and an inter-stimulus interval of 100 msec. Both MK801 (MK) and Apomorphine (APO) induce PPI defects in 14-3-3ζ$^{062+/+}$ mice. In contrast, only APO induces further PPI defects in 14-3-3ζ$^{062-/-}$ mice.
Figure 17:
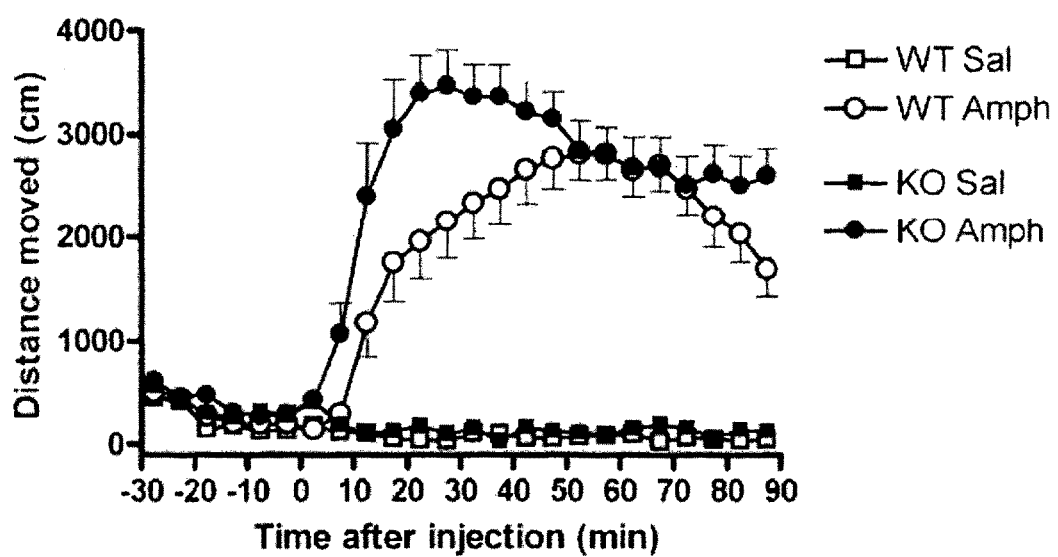
FIG. 17: 14-3-3ζ controls dopaminergic pathways to mediate locomotor activity. 14-3-3ζ$^{062-/-}$ mice (open bars; n=11; 6 male and 5 female) have greater exploratory behaviour at 30 weeks of age than 14-3-3ζ$^{062+/+}$ littermates in an open field test when treated with D-Amphetamine. Sal, saline. Data from male and female mice is pooled in all graphs. Error bars are presented as mean±SEM. *, p<0.05.

Converging clinical and experimental evidence suggest that schizophrenia and related disorders arise from interconnected defects in the dopaminergic and glutamatergic neurotransmitter pathways. The hippocampus has been posited as a key structure in this model as hippocampal pyramidal neurons integrate the glutamatergic and dopaminergic systems. To determine if either neurotransmitter pathway underpins the schizophrenia-like behavioural defects in 14-3-3ζ$^{-/-}$ mice, psychotropic drug induced behavioural studies were undertaken that specifically anatgonise each pathway (FIG. 16). It was found that the NMDA receptor antagonist, MK801, disrupted PPI in wild-type controls but not in 14-3-3ζ$^{-/-}$ mice. In contrast, the dopamine releaser, apomorphine, had a similar effect on PPI in both 14-3-3ζ$^{-/-}$ mice and wild type controls. This indicates that the baseline PPI defect of 14-3-3ζ$^{-/-}$ mice results from deficiencies in the glutamatergic pathway. The hyperdopaminergic hypothesis was also investigated using another dopamine releaser, amphetamine, in the locomoter function test. It was found that an enhanced effect occurred in 14-3-3ζ$^{-/-}$ mice compared to wild-type controls (i.e. a decrease in time to become hyperactive and an increase in distance travelled) indicating that the baseline hyperactivity of 14-3-3ζ$^{-/-}$ mice results from deficiency in the dopaminergic pathway (FIG. 17). Thus, 14-3-3ζ$^{-/-}$ mice have defects in the dopaminergic and glutamatergic neurotransmitter pathways. Given the ability of these drugs to induce similar effects in schizophrenia patients, these findings provide solid support for 14-3-3ζ$^{-/-}$ mice as a model for schizophrenia and related disorders.

Example 3

Figure 18:
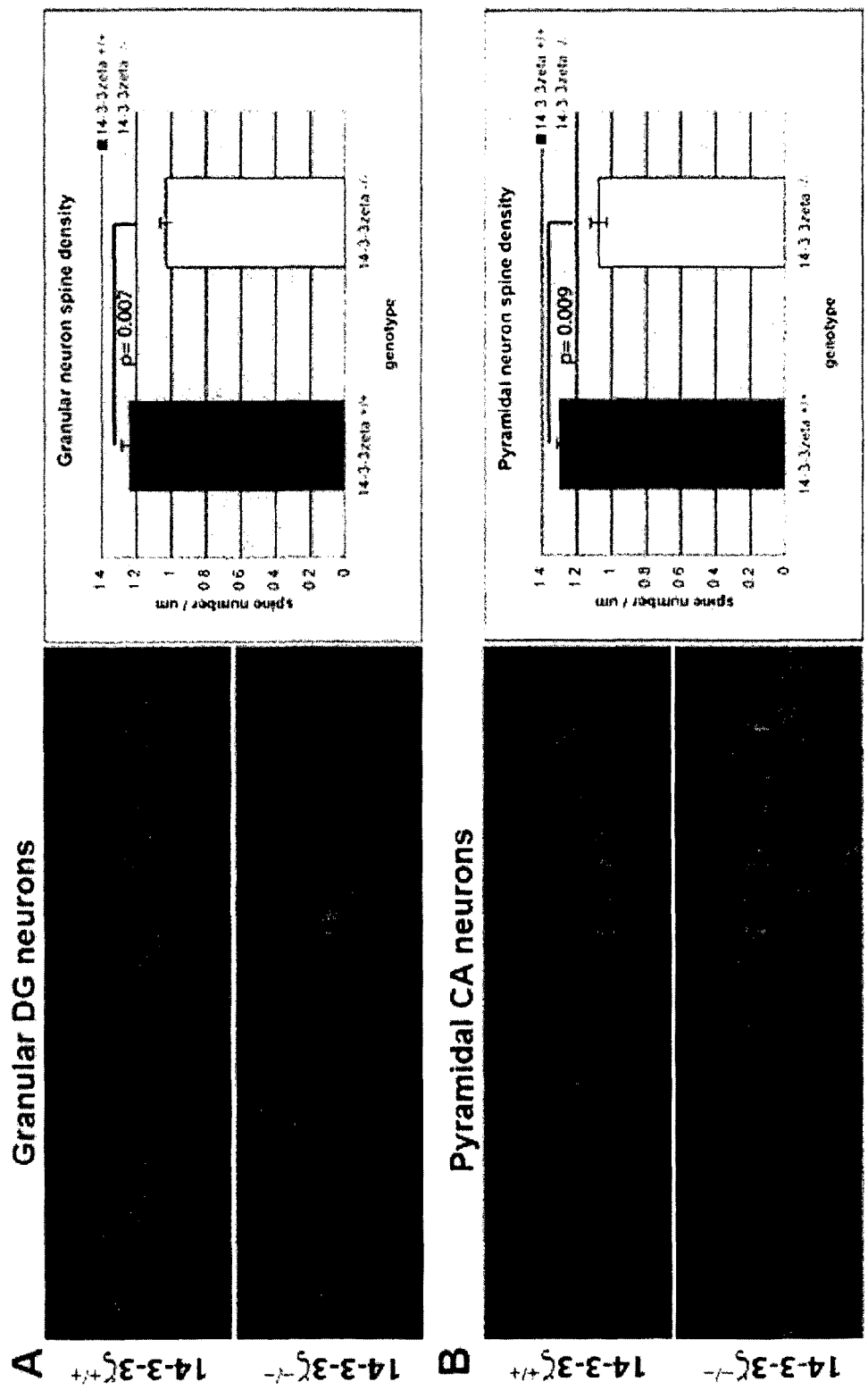
FIG. 18: 14-3-3ζ-deficient mice have reduced spine density.

Reduced dendritic branching and spiny synapses are an anatomical hallmark of schizophrenia and related disorders. Using complimentary techniques such as golgi impregnation, in vitro culture of pyramidal neurons and biolistic labelling, analysis has been performed of dendritic spine numbers and spine size in granular and pyramidal neurons of the hippocampus (FIG. 18). In strong support of the 14-3-3ζ-/- mice as a robust model for schizophrenia and related disorders, significantly reduced spines in the hippocampus were found.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

Bradshaw and Porteous (2010 Dec. 31). "DISC1-binding proteins in neural development, signalling and schizophrenia.". *Neuropharmacology*
Brenner and Lerner. (1992) *PNAS USA* 89:5381-3
Christian R. B et al. (1992) *J. Mol. Biol.* 227:711-718
Clark et al. 2006, *Nature Protocols* 1:2353-2364
Coyle et al. *Behav Brain Res* 2009, 197(1): 210-218
de Bruin et al. *Pharmacol Biochem Behav* 2006; 85(1):253-260
Dere et al. *Neurosci Biobehav Rev* 2006; 30(8):1206-1224
Devlin et al. (1990) *Science* 249:404-406
Eichler et al., *Med. Res. Rev.* 15:481-496 (1995)
Erb et al. (1994) *PNAS USA* 91:11422-11426
Fodor et al., (1991) *Science*, Vol. 251(4995):767-773
Forwood et al. *Hippocampus* 2005; 15(3):347-355
Francis et al., *Curr. Opin. Chem. Biol.*, 2:422-428 (1998)
Fu et al. *Annu Rev Pharmacol Toxicol* 2000; 40:617-647
Gallop et al. (1994) *J. Medicinal Chemistry* 37(9): 1233-1251
Germer et al., *Genome Res.* 10:258-266 (2000)
Gordon et al., *Acc. Chem. Res.* 29:144-154 (1996)
Gordon et al., *J. Med. Chem.* 37:1233-1251 (1994)
Gordon et al., *J. Med. Chem.* 37:1385-1401 (1994)
Guo et al., *Nucleic Acids Res.* 22:5456-5465 (1994)
Guthridge et al. *Blood* 2004; 103(3):820-827

TABLE 1

Primers used for quantitative RT-PCR of 14-3-3 isoforms and for genotyping mice

|  | Forward | Reverse |
|---|---|---|
| 14-3-3 $^{062}$ WT | GAACTTCAGATCTGGTGAC (SEQ ID NO: 2) | GATTGTACTCAAAATGGTGGAC (SEQ ID NO: 3) |
| 14-3-3ζ$^{062}$ KO | GCGTTACTTAAGCTAGCTTGC (SEQ ID NO: 4) | GATTGTACTCAAAATGGTGGAC (SEQ ID NO: 5) |
| 14-3-3~$^{90}$ WT | ACGGCGGGGGGCAGCCAG (SEQ ID NO: 6) | CTCCTGGAAAGATGCGAAC (SEQ ID NO: 7) |
| 14-3-3ζ$^{90}$ KO | GCGTTACTTAAGCTAGCTTGC (SEQ ID NO: 8) | CGCTGGGGACCCCGTGC (SEQ ID NO: 9) |
| Beta | GCAACGATGTGCTGGAGC (SEQ ID NO: 10) | GAGTTGGACACCGTGGTTTG (SEQ ID NO: 11) |
| Epsilon | TACGACGAAATGGTGGAATC (SEQ ID NO: 12) | GCTCAGTTTCAACCATTTGC (SEQ ID NO: 13) |
| Eta | CGAGTCGCGAGCGACATG (SEQ ID NO: 14) | CCCTCCAAGAAGATCGCCTG (SEQ ID NO: 15) |
| Gamma | GCCATGAAGAACGTGACC (SEQ ID NO: 16) | TCTCGTACTGGGTCTCGC (SEQ ID NO: 17) |
| Sigma | TGTGTGCGACACTGTGCTC (SEQ ID NO: 18) | TCGGCTAGGTAGCGGTAGT (SEQ ID NO: 19) |
| Tau | TCGCCATGGAGAAGACCG (SEQ ID NO: 20) | CCGATAGTCCTTGATCAGC (SEQ ID NO: 21) |
| Zeta | GCAACGATGTACTGTCTC (SEQ ID NO: 22) | CTGGTCCACAATTCCTTTC (SEQ ID NO: 23) |

BIBLIOGRAPHY

Aitken A., *Semin Cancer Biol* 2006; 16(3):162-172
Alon et al., *Proc. Natl. Acad. Sci. USA:* 96, 6745-6750, June 1999
Baxter et al. *Neuroscience* 2002; 109(1):5-14
Berg et al. *Nat Rev Neurosci* 2003; 4(9):752-762
Field et al., *Genome Res.* 6:986-994 (1996)
Houghten et al. (1991) *Nature,* 354: 84-88
Houghten et al. (1992) *BioTechniques* 13(3):412-421
Jayawickreme et al. (1994) *PNAS USA* 91:1614-1618
Kaech et al. *Nat Protoc* 2006, 1(5):2406-2415
Kay et al. (1993) *Gene* 128:59-65
Komada et al. *J Vis Exp* 2008; (22)

Lam et al. (1991) *Nature* 354:82-84
Lenstra. (1992) *J. Immun. Methods* 152:149-157
Lister R G, *Psychopharmacology (Berl)* 1987; 92(2):180-185
Maskos and Southern, *Nuc. Acids Res.* 20:1679-84, 1992
Maskos and Southern, *Nuc. Acids Res.* 20:1679-84, 1992
Mattheakis et al. (1994) *PNAS USA* 91:9022-9026
Medynski. (1994) *Bio/Technology* 12:709-710
Middleton et al. *Neuropsychopharmacology* 2005; 30(5): 974-983
Millar et al. 2000, *Hum. Mol. Genet.* 9(9): 1415-23
Moore et al., *BBA,* 1402:239-249, 1988
Nakahira et al. *J Comp Neurol* 2005; 483(3):329-340
Nakata et al., (2009). *Proc Natl Acad Sci USA.* 106(37): 15873-8
Ohlmeyer et al. (1993) *PNAS USA* 90:10922-10926
Pease et al., *Proc. Natl. Acad. Sci. USA* 91(11):5022-5026 (1994)
Rosner et al. *Amino Acids* 2006; 30(1):105-109
Salmon et al. (1993) *PNAS USA* 90:11708-11712
Schiff et al. *Eur J Med Genet* 2010; 53(5):303-308
Scott and Smith. (1990) *Science* 249:386-390
Sik et al. *Behav Brain Res* 2003; 147(1-2):49-54
Smith et al., *Science* 258:1122-1126 (1992)
Sofia, *Molecule. Divers.,* 3:75-94 (1998)
Su et al. *Proc Natl Acad Sci USA* 2011; 108(4):1555-1560
Summers et al. *Pediatr Res* 2006; 59(1): 66-71
Taylor et al., (2003) *Genomics* 81(1):67-77
Tietze et al., *Curr. Biol.,* 2:363-381 (1998)
Toyo-oka et al. *Nat Genet* 2003 July; 34(3): 274-285
Tzivion and Avruch 2002, *J. Biol. Chem.* 277:3061-64
van den Buuse et al. *Int J Neuropsychopharmacol* 2009; 12(10):1383-1393
Walf et al. *Nat Protoc* 2007; 2(2):322-328
Wedemeyer et al., *Clinical Chemistry* 48:9 1398-1405, 2002)
Weissleder et al., *Nature Medicine* 6:351-355, 2000
Wilson and Czarnik, eds., *Combinatorial Chemistry: Synthesis and Application,* John Wiley & Sons, New York (1997).
Winters et al. *J Neurosci* 2005; 25(17):4243-4251
Wong et al. *Schizophr Res* 2005; 78(2-3):137-146
Xing et al. 2000, *EMBO J.* 19:349-58
Yaffe 2002, *FEBS Letts.* 513:53-57

The invention claimed is:

1. A method of detecting 14-3-3ζ protein comprising:
   obtaining a blood sample from a subject; and
   detecting the presence of 14-3-3ζ protein in the blood sample from said subject by contacting the blood sample with an antibody specific for 14-3-3ζ protein and detecting the binding of the 14-3-3ζ protein and the antibody,
   wherein said subject has or is suspected of having schizophrenia, schizotypal personality disorder, psychosis, bipolar disorder, manic depression, affective disorder, schizophreniform, schizoaffective disorders, psychotic depression, autism, drug induced psychosis, delirium, alcohol withdrawal syndrome or dementia induced psychosis.

2. The method according to claim 1, wherein said subject is a human.

\* \* \* \* \*

```
                      SEQUENCE LISTING

<160> NUMBER OF SEQ ID NOS: 23

<210> SEQ ID NO 1
<211> LENGTH: 245
<212> TYPE: PRT
<213> ORGANISM: Homo sapien

<400> SEQUENCE: 1

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220
```

Leu Thr Leu Trp Thr Ser Asp Thr Gln Gly Asp Glu Ala Glu Ala Gly
225                 230                 235                 240

Glu Gly Gly Glu Asn
            245

<210> SEQ ID NO 2
<211> LENGTH: 19
<212> TYPE: DNA
<213> ORGANISM: murine

<400> SEQUENCE: 2
gaacttcaga tctggtgac                                              19

<210> SEQ ID NO 3
<211> LENGTH: 22
<212> TYPE: DNA
<213> ORGANISM: murine

<400> SEQUENCE: 3
gattgtactc aaaatggtgg ac                                          22

<210> SEQ ID NO 4
<211> LENGTH: 21
<212> TYPE: DNA
<213> ORGANISM: murine

<400> SEQUENCE: 4
gcgttactta agctagcttg c                                           21

<210> SEQ ID NO 5
<211> LENGTH: 22
<212> TYPE: DNA
<213> ORGANISM: murine

<400> SEQUENCE: 5
gattgtactc aaaatggtgg ac                                          22

<210> SEQ ID NO 6
<211> LENGTH: 18
<212> TYPE: DNA
<213> ORGANISM: murine

<400> SEQUENCE: 6
acggcggggg gcagccag                                               18

<210> SEQ ID NO 7
<211> LENGTH: 19
<212> TYPE: DNA
<213> ORGANISM: murine

<400> SEQUENCE: 7
ctcctggaaa gatgcgaac                                              19

<210> SEQ ID NO 8
<211> LENGTH: 21
<212> TYPE: DNA
<213> ORGANISM: murine

<400> SEQUENCE: 8
gcgttactta agctagcttg c                                           21

<210> SEQ ID NO 9

```
<211> LENGTH: 17
<212> TYPE: DNA
<213> ORGANISM: murine

<400> SEQUENCE: 9
cgctggggac cccgtgc                                                    17

<210> SEQ ID NO 10
<211> LENGTH: 18
<212> TYPE: DNA
<213> ORGANISM: murine

<400> SEQUENCE: 10
gcaacgatgt gctggagc                                                   18

<210> SEQ ID NO 11
<211> LENGTH: 20
<212> TYPE: DNA
<213> ORGANISM: murine

<400> SEQUENCE: 11
gagttggaca ccgtggtttg                                                 20

<210> SEQ ID NO 12
<211> LENGTH: 20
<212> TYPE: DNA
<213> ORGANISM: murine

<400> SEQUENCE: 12
tacgacgaaa tggtggaatc                                                 20

<210> SEQ ID NO 13
<211> LENGTH: 20
<212> TYPE: DNA
<213> ORGANISM: murine

<400> SEQUENCE: 13
gctcagtttc aaccatttgc                                                 20

<210> SEQ ID NO 14
<211> LENGTH: 18
<212> TYPE: DNA
<213> ORGANISM: murine

<400> SEQUENCE: 14
cgagtcgcga gcgacatg                                                   18

<210> SEQ ID NO 15
<211> LENGTH: 20
<212> TYPE: DNA
<213> ORGANISM: murine

<400> SEQUENCE: 15
ccctccaaga agatcgcctg                                                 20

<210> SEQ ID NO 16
<211> LENGTH: 18
<212> TYPE: DNA
<213> ORGANISM: murine

<400> SEQUENCE: 16
gccatgaaga acgtgacc                                                   18
```

```
<210> SEQ ID NO 17
<211> LENGTH: 18
<212> TYPE: DNA
<213> ORGANISM: murine

<400> SEQUENCE: 17
tctcgtactg ggtctcgc                                                 18

<210> SEQ ID NO 18
<211> LENGTH: 19
<212> TYPE: DNA
<213> ORGANISM: murine

<400> SEQUENCE: 18
tgtgtgcgac actgtgctc                                                19

<210> SEQ ID NO 19
<211> LENGTH: 19
<212> TYPE: DNA
<213> ORGANISM: murine

<400> SEQUENCE: 19
tcggctaggt agcggtagt                                                19

<210> SEQ ID NO 20
<211> LENGTH: 18
<212> TYPE: DNA
<213> ORGANISM: murine

<400> SEQUENCE: 20
tcgccatgga gaagaccg                                                 18

<210> SEQ ID NO 21
<211> LENGTH: 19
<212> TYPE: DNA
<213> ORGANISM: murine

<400> SEQUENCE: 21
ccgatagtcc ttgatcagc                                                19

<210> SEQ ID NO 22
<211> LENGTH: 18
<212> TYPE: DNA
<213> ORGANISM: murine

<400> SEQUENCE: 22
gcaacgatgt actgtctc                                                 18

<210> SEQ ID NO 23
<211> LENGTH: 19
<212> TYPE: DNA
<213> ORGANISM: murine

<400> SEQUENCE: 23
ctggtccaca attcctttc                                                19
```